US012576145B2

(12) United States Patent
Garrison et al.

(10) Patent No.: US 12,576,145 B2
(45) Date of Patent: Mar. 17, 2026

(54) CRIMEAN-CONGO HEMORRHAGIC FEVER VIRUS M-SEGMENT NUCLEIC ACID VACCINE AND METHODS OF USE AND PRODUCTION

(71) Applicant: THE GOVERNMENT OF THE UNITED STATES AS REPRESENTED BY THE SECRETARY OF THE ARMY, Fort Detrick, MD (US)

(72) Inventors: Aura R. Garrison, Knoxville, MD (US); Charles J. Shoemaker, Stephens City, VA (US); John J. Suschak, III, Damascus, MD (US)

(73) Assignee: The Government of the United States, as Represented by the Secretary of the Army, Ft. Detrick, MD (US)

( * ) Notice: Subject to any disclaimer, the term of this patent is extended or adjusted under 35 U.S.C. 154(b) by 332 days.

(21) Appl. No.: 18/029,576

(22) PCT Filed: Sep. 30, 2021

(86) PCT No.: PCT/US2021/052860
§ 371 (c)(1),
(2) Date: Mar. 30, 2023

(87) PCT Pub. No.: WO2022/072622
PCT Pub. Date: Apr. 7, 2022

(65) Prior Publication Data
US 2025/0205327 A1      Jun. 26, 2025

Related U.S. Application Data

(60) Provisional application No. 63/085,186, filed on Sep. 30, 2020.

(51) Int. Cl.
| | |
|---|---|
| *A61K 39/00* | (2006.01) |
| *A61K 39/12* | (2006.01) |
| *A61P 31/14* | (2006.01) |
| *C12N 7/00* | (2006.01) |
| *C12N 15/86* | (2006.01) |

(52) U.S. Cl.
CPC ............. *A61K 39/12* (2013.01); *A61P 31/14* (2018.01); *C12N 7/00* (2013.01); *C12N 15/86* (2013.01); *A61K 2039/53* (2013.01); *A61K 2039/545* (2013.01); *A61K 2039/572* (2013.01); *A61K 2039/575* (2013.01); *C12N 2760/12034* (2013.01)

(58) Field of Classification Search
CPC .......... A61K 2039/53; A61K 2039/545; A61K 39/12; A61P 31/14; C07K 14/005
See application file for complete search history.

(56) References Cited

FOREIGN PATENT DOCUMENTS

| | | |
|---|---|---|
| WO | 2019038332 A1 | 2/2019 |
| WO | 2020146421 A1 | 7/2020 |

OTHER PUBLICATIONS

PCT Search Report & Written Opinion, PCT/US2021/052860, mailed Feb. 28, 2023, 11 pages.
Aligholipour Farzani, Touraj et al., "Immunological Analysis of a CCHFV mRNA Vaccine Candidate in Mouse Models", Vaccines, 2019, vol. 7, No. 115, 17 pages.
Bertolotti-Ciarlet, Andrea et al., "Cellular Localization and Antigenic Characterization of Crimean-Congo Hemorrhagic Virus Glycoproteins", Journal of Virology, May 2005, p. 6152-6161, vol. 79, No. 10.
Buttigieg, Karen R. et al., "A Novel Vaccine against Crimean-Congo Hemorrhagic Fever Protects 100% of Animals against Lethal Challenge in a Mouse Model", Plos One, 2014, vol. 9, No. 3, 14 pages.
Canakoglu, Nurettin et al., "Immunization of Knock-Out $\alpha/\beta$ Interferon Receptor Mice against High Lethal Dose of Crimean-Congo Hemorrhagic Fever Virus with a Cell Culture Based Vaccine", PLOS Neglected Tropical Diseases, 2015, 14 pages.
Conger, Nicholas G. et al., Health Care Response to CCHF in US Soldier and Nosocomial Transmission to Health Care Providers, Germany, Emerging Infectious Diseases 2009, Jan. 2015, vol. 21, No. 1, pp. 23-31.

(Continued)

*Primary Examiner* — Barry A Chestnut
(74) *Attorney, Agent, or Firm* — Timothy H. Van Dyke; Wolter Van Dyke Davis, PLLC

(57) ABSTRACT

Crimean-Congo hemorrhagic fever virus (CCHFV) is a tick-borne virus that causes severe hemorrhagic fever disease in humans. Currently, no licensed CCHF vaccines exist, and the protective epitopes remain unclear. Here, we tested a DNA vaccine expressing the M-segment glycoprotein precursor gene (GPC) of the laboratory CCHFV strain CCHFV-IbAr 10200 (CCHFV-M10200). Increasing the dose of CCHFV-M 10200 provides complete protection from homologous CCHFV challenge in mice, and significant (80%) protection from challenge with the clinically relevant, heterologous CCHFV-Afg09-2990 strain. We also report complete protection from CCHFV-Afg09-2990 challenge following vaccination with a CCHFV-Afg09-2990 GPC expressing DNA vaccine (CCHFV-M Afgog). Finally, we show that the non-structural M-segment protein, GP38, influences CCHF vaccine immunogenicity and provides significant protection from homologous CCHFV challenge. Our results demonstrate that M-segment DNA vaccines elicit protective CCHF immunity and further illustrate the immunorelevance of GP38.

27 Claims, 15 Drawing Sheets
Specification includes a Sequence Listing.

(56)                    References Cited

OTHER PUBLICATIONS

The National Academies Press, "Guide For The Care and Use of Laboratory Animals", 2011, 246 pages.

Dowall, Stuart D. et al., "Protective effects of a Modified Vaccinia Ankara-based vaccine candidate against Crimean-Congo Haemorrhagic Fever virus require both cellular and humoral responses", Plos One, 2016, vol. 11, No. 6, 13 pages.

Fritzen, Amanda et al., "Epitope-mapping of the glycoprotein from Crimean-Congo hemorrhagic fever virus using a microarray approach", PLoS Negl Trop Dis, 2018, vol. 12, No. 7, 15 pages.

Garrison, Aura R. et al., "A DNA vaccine for Crimean-Congo hemorrhagic fever protects against disease and death in two lethal mouse models", PLoS Negl Trop Dis, 2017, vol. 11, No. 9, 19 pages.

Golden, Joseph W. et al., "GP38-targeting monoclonal antibodies protect adult mice against lethal Crimean-Congo hemorrhagic fever virus infection", Sci. Adv., 2019, vol. 5, 14 pages.

Hinkula, Jorma et al., "Immunization with DNA Plasmids Coding for Crimean-Congo Hemorrhagic Fever Virus Capsid and Envelope Proteins and/or Virus-Like Particles Induces Protection and Survival in Challenged Mice", Journal of Virology, May 2017, vol. 91, Issue 10, 19 pages.

Kortekaas, Jeroen et al., "Crimean-Congo Hemorrhagic Fever Virus Subunit Vaccines Induce High Levels of Neutralizing Antibodies But No Protection in STAT1 Knockout Mice", Vector-Borne and Zoonotic Diseases, 2015, vol. 15, No. 12, pp. 759-764.

Lindquist, Michael E. et al., "Exploring Crimean-Congo Hemorrhagic Fever Virus-Induced Hepatic Injury Using Antibody-Mediated Type I Interferon Blockade in Mice", Journal of Virology, Nov. 2018, vol. 92, Issue 21, 22 pages.

Mishra, Akaash K. et al., "Structure and Characterization of Crimean-Congo Hemorrhagic Fever Virus GP38", Journal of Virology, Apr. 2020, vol. 94, Issue 8, 13 pages.

Rodriguez, Sergio E. et al., "Vesicular Stomatitis Virus-Based Vaccine Protects Mice against Crimean-Congo Hemorrahagic Fever", Scientific Reports, 2019, vol. 9, No. 7755, 14 pages.

Scholte, Florine E. M. et al., "Single-dose replicon particle vaccine provides complete protection against Crimean-Congo hemorrhagic fever virus in mice", Emerging Microbes & Infections, 2019, vol. 8, 575-578.

Whalen, Robert G., "DNA Vaccines for Emerging Infectious Diseases: What If?", Emerging Infectious Diseases, Jul.-Sep. 1996, vol. 2, No. 3, pp. 168-175.

WHO, "Blueprint for R&D preparedness and response to public health emergencies due to highly infectious pathogens", Dec. 8-9, 2015, 7 pages.

WHO, "2018 Annual review of diseases prioritized under the Research and Development Blueprint", Feb. 6-7, 3 pages.

Zivcec, Marko et al., "Nucleocapsid protein-based vaccine provides protection in mice against lethal Crimean-Congo hemorrhagic fever virus challenge", PLOS Neglected Tropical Diseases, Jul. 16, 2018, vol. 12, No. 7, 14 pages.

Bente, Dennis A. et al., "Crimean-Congo hemorrhagic fever: History, epidemiology, pathogenesis, clinical syndrome and genetic diversity", Antiviral Research, 2013, vol. 100, pp. 159-189.

Swanepoel, R. et al., "The Clinical Pathology of Crimean-Congo Hemorrhagic Fever", Reviews of Infectious Diseases, May-Jun. 1989, vol. 11, Supplement 4, pp. S794-S800.

Shepherd, A.J. et al., "Antibody Response in Crimean-Congo Hemorrhagic Fever", Reviews of Infectious Diseases, May-Jun. 1989, vol. 11, Supplement 4, 99. S801-S806.

Spik, Kristin et al., "Immunogenicity of combination DNA vaccines for Rift Valley fever virus, tick-borne encephalitis virus, Hantaan virus, and Crimean Congo hemorrhagic fever virus", Vaccine, 2006, vol. 24, pp. 4657-4666.

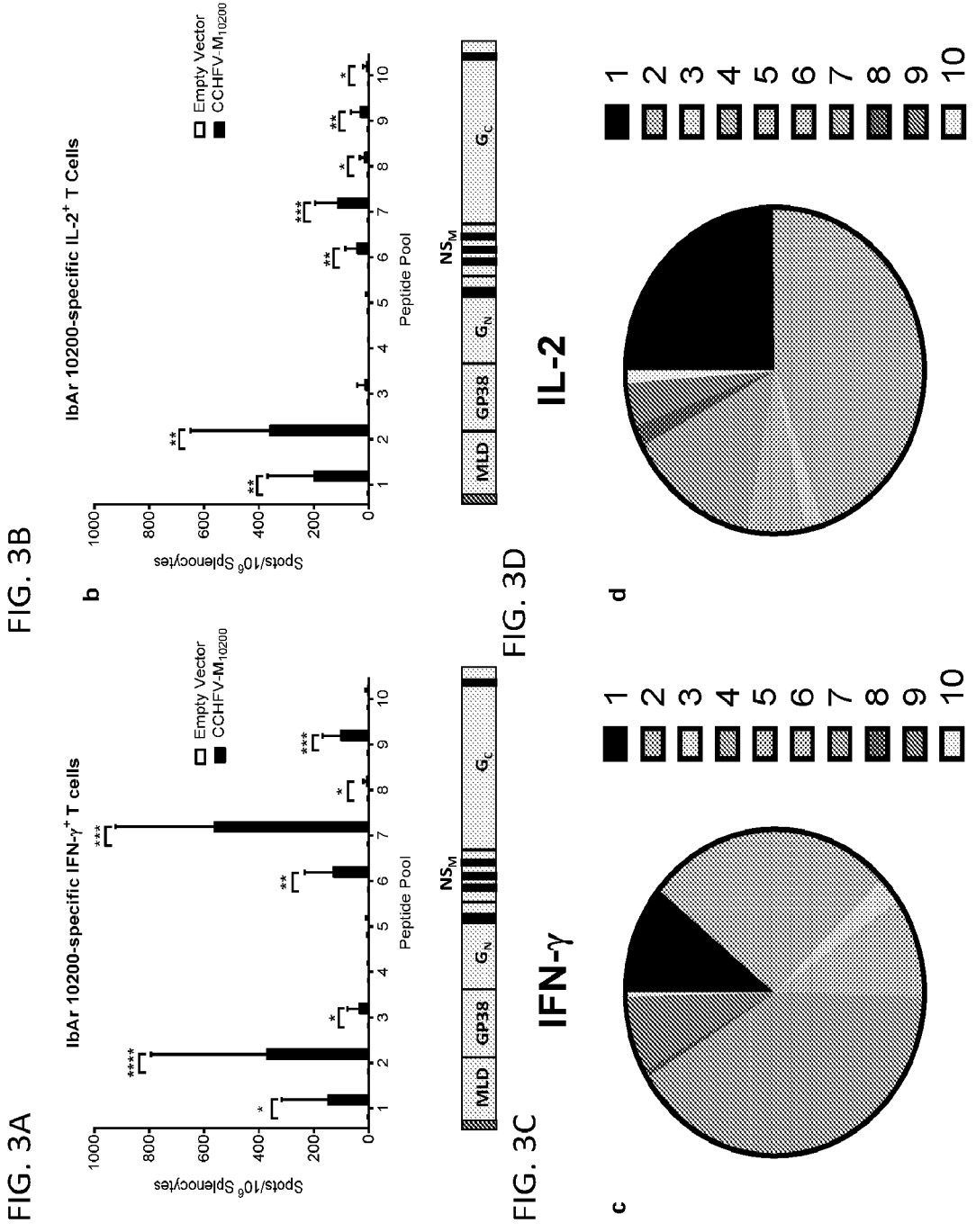

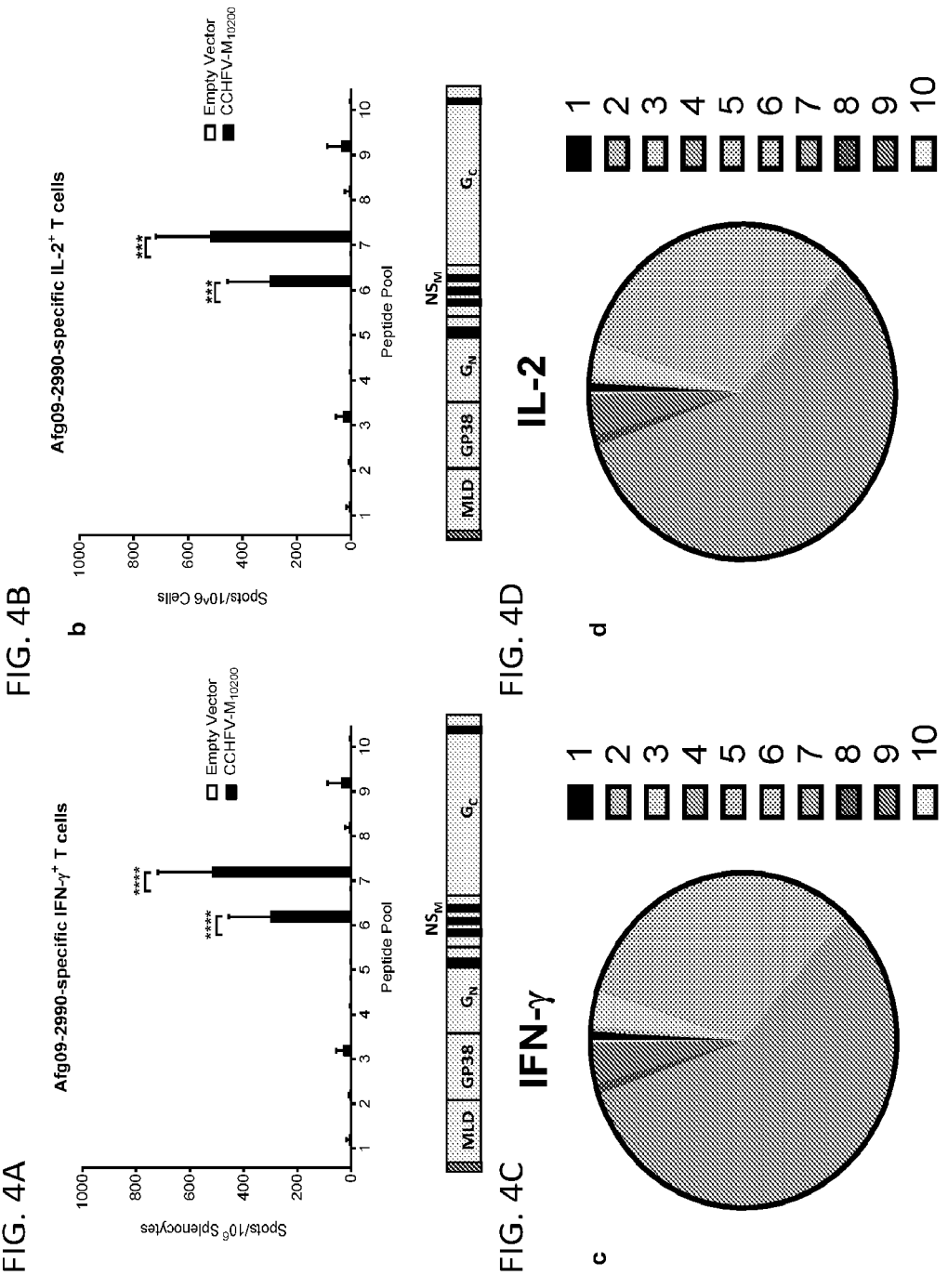

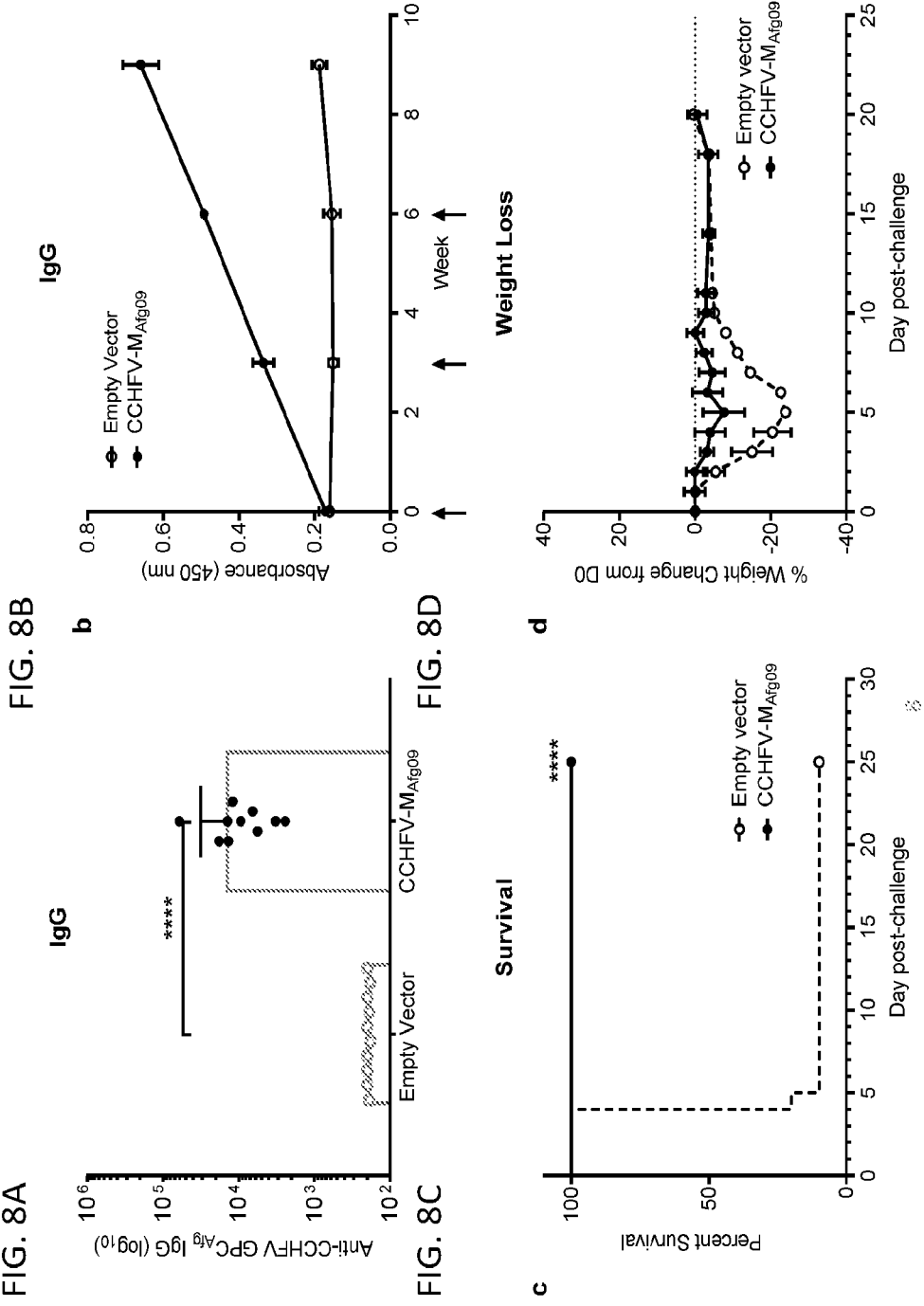

Figure 12:
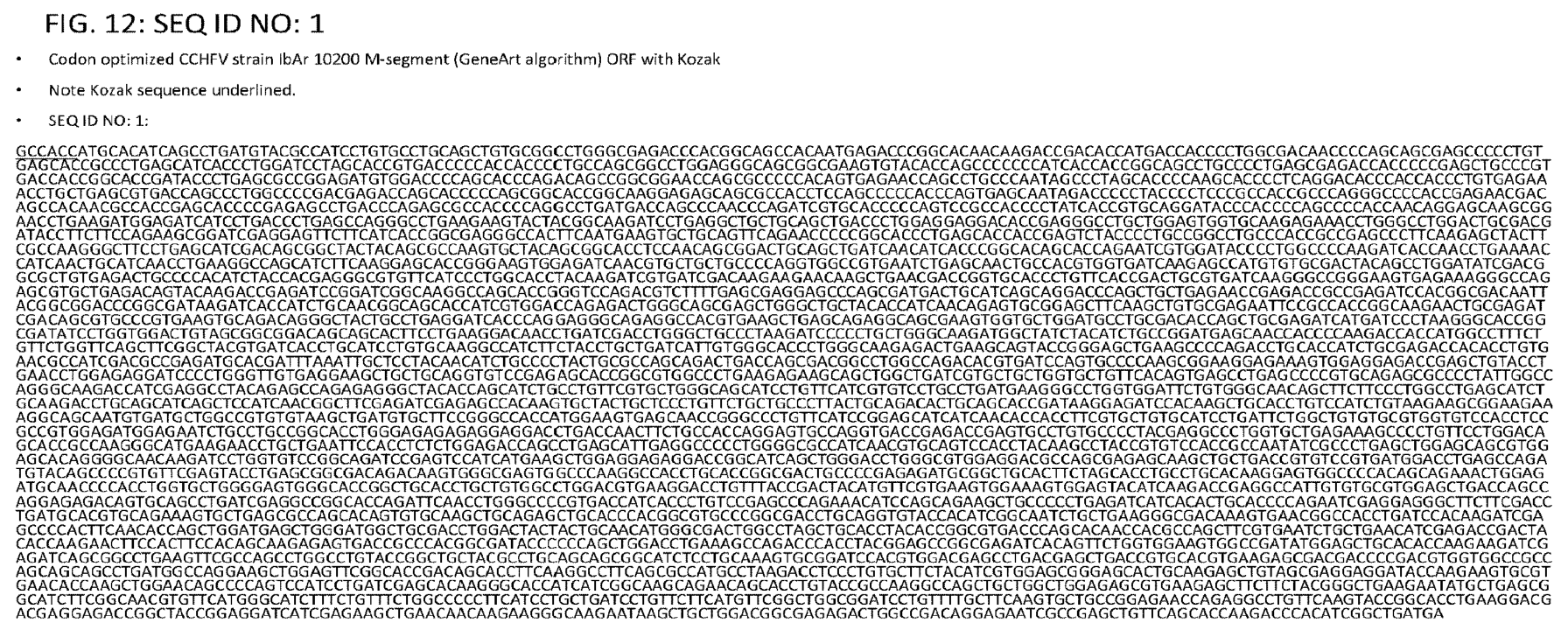

FIG. 12: SEQ ID NO: 1

- Codon optimized CCHFV strain IbAr 10200 M-segment (GeneArt algorithm) ORF with Kozak
- Note Kozak sequence underlined.
- SEQ ID NO: 1:

FIG. 13

WRG7077 with CCHFV strain IbAr 10200 codon optimized M segment (GeneArt algorithm). Note that the antibiotic resistance in Kanamycin. The NotI and BglII cloning sites are in bold. SEQ ID NO: 2:

FIG. 14

- CCHFV Afg09-2990 M-segment codon optimized sequence using ATUM
- Note Kozak sequence underlined.
- SEQ ID NO: 3:

FIG. 15

CCHFV-Afg09-2990 codon optimized M in pWRG7077 (ATUM codon optimization algorithm). Note that the antibiotic resistance in Kanamycin. The NotI and BglII cloning sites are in bold. SEQ ID NO: 4:

SEQUENCE LISTING

<160> NUMBER OF SEQ ID NOS: 4

<210> SEQ ID NO 1
<211> LENGTH: 5064
<212> TYPE: DNA
<213> ORGANISM: Artificial Sequence
<220> FEATURE:

<223> OTHER INFORMATION: Synthesized

<400> SEQUENCE: 1

```
gccaccatgc acatcagcct gatgtacgcc atcctgtgcc tgcagctgtg cggcctgggc        60
gagacccacg gcagccacaa tgagacccgg cacaacaaga ccgacaccat gaccaccect       120 ggcgacaacc ccagcagcga gcccctgtg agcaccgccc tgagcatcac cctggatcct       180
agcaccgtga cccccaccac ccctgccagc ggcctggagg gcagcggcga agtgtacacc       240 agcccccca tcaccaccgg cagcctgccc ctgagcgaga ccacccccga gctgcccgtg       300
accaccggca ccgataccct gagcgccgga gatgtggacc ccagcaccca gacagccggc       360
ggaaccagcg cccccacagt gagaaccagc ctgcccaata gccctagcac cccaagcacc       420
cctcaggaca cccaccaccc tgtgagaaac ctgctgagcg tgaccagccc tggccccgac       480
gagaccagca cccccagcgg caccggcaag gagagcagcg ccacctccag cccccaccca       540
gtgagcaata gacccctac ccctcccgcc accgcccagg gccccaccga gaacgacagc       600
cacaacgcca ccgagcaccc cgagagcctg acccagagcg ccacccccagg cctgatgacc       660 agcccaaccc agatcgtgca ccccagtcc gccacccta tcaccgtgca ggatacccac       720
cccagcccca ccaacaggag caagcggaac ctgaagatgg agatcatcct gaccctgagc       780
cagggcctga agaagtacta cggcaagatc ctgaggctgc tgcagctgac cctggaggag       840
gacaccgagg gcctgctgga gtggtgcaag agaaacctgg gcctggactg cgacgatacc       900
ttcttccaga gcggatcga ggagttcttc atcaccggcg agggccactt caatgaagtg       960
ctgcagttca gaaccccgg caccctgagc accaccgagt ctaccctgc cggcctgccc      1020 accgccgagc ccttcaagag ctacttcgcc aagggcttcc tgagcatcga cagcggctac      1080
tacagcgcca agtgctacag cggcacctcc aacagcggac tgcagctgat caacatcacc      1140
cggcacagca ccagaatcgt ggatacccct ggccccaaga tcaccaacct gaaaaccatc      1200
aactgcatca acctgaaggc cagcatcttc aaggagcacc gggaagtgga gatcaacgtg      1260
ctgctgcccc aggtggccgt gaatctgagc aactgccacg tggtgatcaa gagccatgtg      1320
tgcgactaca gcctggatat cgacggcgct gtgagactgc cccacatcta ccacgagggc      1380
gtgttcatcc ctggcaccta caagatcgtg atcgacaaga agaacaagct gaacgaccgg      1440
tgcaccctgt tcaccgactg cgtgatcaag ggccgggaag tgagaaaggg ccagagcgtg      1500
ctgagacagt acaagaccga gatccggatc ggcaaggcca gcaccgggtc cagacgtctt      1560
ttgagcgagg agcccagcga tgactgcatc agcaggaccc agctgctgag aaccgagacc      1620
gccgagatcc acggcgacaa ttacggcgga cccggcgata agatcaccat ctgcaacggc      1680
agcaccatcg tggaccagag actgggcagc gagctgggct gctacaccat caacagagtg      1740
cggagcttca gctgtgcga gaattccgcc accggcaaga actgcgagat cgacagcgtg      1800
cccgtgaagt gcagacaggg ctactgcctg aggatcaccc aggagggcag aggccacgtg      1860
aagctgagca gaggcagcga agtggtgctg gatgcctgcg acaccagctg cgagatcatg      1920
atccctaagg gcaccggcga tatcctggtg gactgtagcg gcggacagca gcacttcctg      1980
aaggacaacc tgatcgacct gggctgccct aagatccccc tgctgggcaa gatggctatc      2040
tacatctgcc ggatgagcaa ccaccccaag accaccatgg cctttctgtt ctggttcagc      2100
ttcggctacg tgatcacctg catcctgtgc aaggccatct tctacctgct gatcattgtg      2160
ggcaccctgg gcaagagact gaagcagtac cgggagctga agccccagac ctgcaccatc      2220
tgcgagacca cacctgtgaa cgccatcgac gccgagatgc acgatttaaa ttgctcctac      2280
```

-continued

```
aacatctgcc cctactgcgc cagcagactg accagcgacg gcctggccag acacgtgatc   2340
cagtgcccca agcggaagga gaaagtggag gagaccgagc tgtacctgaa cctggagagg   2400
atcccctggg ttgtgaggaa gctgctgcag gtgtccgaga gcaccggcgt ggccctgaag   2460
agaagcagct ggctgatcgt gctgctggtg ctgttcacag tgagcctgag ccccgtgcag   2520 agcgcccta ttggccaggg caagaccatc gaggcctaca gagccagaga gggctacacc    2580
agcatctgcc tgttcgtgct gggcagcatc ctgttcatcg tgtcctgcct gatgaagggc   2640
ctggtggatt ctgtgggcaa cagcttcttc cctggcctga gcatctgcaa gacctgcagc   2700
atcagctcca tcaacggctt cgagatcgag agccacaagt gctactgctc cctgttctgc   2760
tgcccttact gcagacactg cagcaccgat aaggagatcc acaagctgca cctgtccatc   2820
tgtaagaagc ggaagaaagg cagcaatgtg atgctggccg tgtgtaagct gatgtgcttc   2880
cgggccacca tggaagtgag caaccgggcc ctgttcatcc ggagcatcat caacaccacc   2940
ttcgtgctgt gcatcctgat tctggctgtg tgcgtggtgt ccacctccgc cgtggagatg   3000
gagaatctgc ctgccggcac ctgggagaga gaggaggacc tgaccaactt ctgccaccag   3060
gagtgccagg tgaccgagac cgagtgcctg tgcccctacg aggccctggt gctgagaaag   3120
cccctgttcc tggacagcac cgccaagggc atgaagaacc tgctgaattc cacctctctg   3180
gagaccagcc tgagcattga ggccccctgg ggcgccatca cgtgcagtc cacctacaag    3240 cctaccgtgt ccaccgccaa tatcgccctg agctggagca gcgtggagca cagggtcaac   3300
aagatcctgg tgtccggcag atccgagtcc atcatgaagc tggaggagag gaccggcatc   3360
agctgggacc tgggcgtgga ggacgccagc gagagcaagc tgctgaccgt gtccgtgatg   3420
gacctgagcc agatgtacag ccccgtgttc gagtacctga gcggcgacag acaagtgggc   3480
gagtggccca aggccacctg caccggcgac tgcccccgaga gatgcggctg cacttctagc   3540
acctgcctgc acaaggagtg gccccacagc agaaactgga gatgcaaccc cacctggtgc   3600
tggggagtgg gcaccggctg cacctgctgt ggcctggacg tgaaggacct gtttaccgac   3660
tacatgttcg tgaagtggaa agtggagtac atcaagaccg aggccattgt gtgcgtggag   3720
ctgaccagcc aggagagaca gtgcagcctg atcgaggccg gcaccagatt caacctgggc   3780
cccgtgacca tcaccctgtc cgagcccaga aacatccagc agaagctgcc ccctgagatc   3840
atcacactgc accccagaat cgaggagggc ttcttcgacc tgatgcacgt gcagaaagtg   3900
ctgagcgcca gcacagtgtg caagctgcag agctgcaccc acggcgtgcc cggcgacctg   3960
caggtgtacc acatcggcaa tctgctgaag ggcgacaaag tgaacggcca cctgatccac   4020
aagatcgagc cccacttcaa caccagctgg atgagctggg atggctgcga cctggactac   4080
tactgcaaca tgggcgactg cctagctgc acctacaccg cgtgaccca gcacaaccac     4140 gccagcttcg tgaatctgct gaacatcgag accgactaca ccaagaactt ccacttccac   4200
agcaagagag tgaccgccca cggcgatacc ccccagctgg acctgaaagc cagacccacc   4260
tacggagccg gcgagatcac agttctggtg gaagtggccg atatggagct gcacaccaag   4320
aagatcgaga tcagcggcct gaagttcgcc agcctggcct gtaccggctg ctacgcctgc   4380
agcagcggca tctcctgcaa agtgcggatc cacgtggaca gcctgacga gctgaccgtg    4440 cacgtgaaga gcgacgaccc cgacgtggtg gccgccagca gcagcctgat ggccaggaag   4500
ctggagttcg gcaccgacag cacccttcaag gccttcagcg ccatgcctaa gacctccctg   4560
tgcttctaca tcgtggagcg ggagcactgc aagagctgta gcgaggagga taccaagaag   4620
```

-continued

```
tgcgtgaaca ccaagctgga acagccccag tccatcctga tcgagcacaa gggcaccatc     4680
atcggcaagc agaacagcac ctgtaccgcc aaggccagct gctggctgga gagcgtgaag     4740
agcttcttct acgggctgaa gaatatgctg agcggcatct tcggcaacgt gttcatgggc     4800
atctttctgt ttctggcccc cttcatcctg ctgatcctgt tcttcatgtt cggctggcgg     4860
atcctgtttt gcttcaagtg ctgccggaga accagaggcc tgttcaagta ccggcacctg     4920
aaggacgacg aggagaccgg ctaccggagg atcatcgaga agctgaacaa caagaagggc     4980
aagaataagc tgctggacgg cgagagactg gccgacagga gaatcgccga gctgttcagc     5040
accaagaccc acatcggctg atga                                           5064

<210> SEQ ID NO 2
<211> LENGTH: 9398
<212> TYPE: DNA
<213> ORGANISM: Artificial Sequence
<220> FEATURE:
<223> OTHER INFORMATION: Plasmid

<400> SEQUENCE: 2
gggggggggg ggcgctgagg tctgcctcgt gaagaaggtg ttgctgactc ataccaggcc       60
tgaatcgccc catcatccag ccagaaagtg agggagccac ggttgatgag agctttgttg      120
taggtggacc agttggtgat tttgaacttt tgctttgcca cggaacggtc tgcgttgtcg      180
ggaagatgcg tgatctgatc cttcaactca gcaaaagttc gatttattca acaaagccgc      240
cgtcccgtca agtcagcgta atgctctgcc agtgttacaa ccaattaacc aattctgatt      300
agaaaaactc atcgagcatc aaatgaaact gcaatttatt catatcagga ttatcaatac      360
catatttttg aaaaagccgt ttctgtaatg aaggagaaaa ctcaccgagg cagttccata      420
ggatggcaag atcctggtat cggtctgcga ttccgactcg tccaacatca atacaaccta      480
ttaatttccc ctcgtcaaaa ataaggttat caagtgagaa atcaccatga gtgacgactg      540
aatccggtga gaatggcaaa agcttatgca tttctttcca gacttgttca acaggccagc      600
cattacgctc gtcatcaaaa tcactcgcat caaccaaacc gttattcatt cgtgattgcg      660
cctgagcgag acgaaatacg cgatcgctgt taaaaggaca attacaaaca ggaatcgaat      720
gcaaccggcg caggaacact gccagcgcat caacaatatt ttcacctgaa tcaggatatt      780
cttctaatac ctggaatgct gttttcccgg ggatcgcagt ggtgagtaac catgcatcat      840
caggagtacg gataaaatgc ttgatggtcg gaagaggcat aaattccgtc agccagttta      900
gtctgaccat ctcatctgta acatcattgg caacgctacc tttgccatgt ttcagaaaca      960
actctggcgc atcgggcttc ccatacaatc gatagattgt cgcacctgat tgcccgacat     1020
tatcgcgagc ccatttatac ccatataaat cagcatccat gttggaattt aatcgcggcc     1080
tcgagcaaga cgtttcccgt tgaatatggc tcataacacc ccttgtatta ctgtttatgt     1140
aagcagacag ttttattgtt catgatgata tattttttatc ttgtgcaatg taacatcaga     1200
gattttgaga cacaacgtgg ctttccccccc cccccggca tgcctgcagg tcgacaatat     1260
tggctattgg ccattgcata cgttgtatct atatcataat atgtacattt atattggctc     1320
atgtccaata tgaccgccat gttgacattg attattgact agttattaat agtaatcaat     1380
tacggggtca ttagttcata gcccatatat ggagttccgc gttacataac ttacggtaaa     1440
tggcccgcct ggctgaccgc ccaacgaccc ccgcccattg acgtcaataa tgacgtatgt     1500
tcccatagta acgccaatag ggactttcca ttgacgtcaa tgggtggagt atttacggta     1560
aactgcccac ttggcagtac atcaagtgta tcatatgcca agtccgcccc ctattgacgt     1620
```

-continued

```
caatgacggt aaatggcccg cctggcatta tgcccagtac atgaccttac gggactttcc   1680
tacttggcag tacatctacg tattagtcat cgctattacc atggtgatgc ggttttggca   1740
gtacaccaat gggcgtggat agcggtttga ctcacgggga tttccaagtc tccaccccat   1800
tgacgtcaat gggagtttgt tttggcacca aaatcaacgg gactttccaa aatgtcgtaa   1860
taaccccgcc ccgttgacgc aaatgggcgg taggcgtgta cggtgggagg tctatataag   1920
cagagctcgt ttagtgaacc gtcagatcgc ctggagacgc catccacgct gttttgacct   1980
ccatagaaga caccgggacc gatccagcct ccgcggccgg gaacggtgca ttggaacgcg   2040
gattccccgt gccaagagtg acgtaagtac cgcctataga ctctataggc acaccccttt   2100
ggctcttatg catgctatac tgtttttggc ttggggccta tacaccccg cttccttatg   2160 ctataggtga tggtatagct tagcctatag gtgtgggtta ttgaccatta ttgaccactc   2220
ccctattggt gacgatactt ccattacta atccataaca tggctctttg ccacaactat   2280
ctctattggc tatatgccaa tactctgtcc ttcagagact gacacggact ctgtatttt    2340 acaggatggg gtcccatttt ttatttacaa attcacatat acaacaacgc cgtcccccgt   2400
gcccgcagtt tttattaaac atagcgtggg atctccacgc gaatctcggg tacgtgttcc   2460
ggacatgggc tcttctccgg tagcggcgga gcttccacat ccgagccctg gtcccatgcc   2520
tccagcggct catggtcgct cggcagctcc ttgctcctaa cagtggaggc cagacttagg   2580
cacagcacaa tgcccaccac caccagtgtg ccgcacaagg ccgtggcggt agggtatgtg   2640
tctgaaaatg agctcggaga ttgggctcgc accgctgacg cagatggaag acttaaggca   2700
gcggcagaag aagatgcagg cagctgagtt gttgtattct gataagagtc agaggtaact   2760
cccgttgcgg tgctgttaac ggtggagggc agtgtagtct gagcagtact cgttgctgcc   2820
gcgcgcgcca ccagacataa tagctgacag actaacagac tgttcctttc catgggtctt   2880
ttctgcagtc accgtccaag cttgcggccg cgccaccatg cacatcagcc tgatgtacgc   2940
catcctgtgc ctgcagctgt gcggcctggg cgagacccac ggcagccaca atgagacccg   3000
gcacaacaag accgacacca tgaccacccc tggcgacaac cccagcagcg agccccctgt   3060
gagcaccgcc ctgagcatca ccctggatcc tagcaccgtg acccccacca cccctgccag   3120
cggcctggag ggcagcggcg aagtgtacac cagccccccc atcaccaccg gcagcctgcc   3180
cctgagcgag accacccccg agctgcccgt gaccaccggc accgataccc tgagcgccgg   3240
agatgtggac cccagcaccc agacagccgg cggaaccagc gcccccacag tgagaaccag   3300
cctgcccaat agccctagca ccccaagcac ccctcaggac acccaccacc ctgtgagaaa   3360
cctgctgagc gtgaccagcc ctggccccga cgagaccagc accccagcg gcaccggcaa    3420 ggagagcagc gccacctcca gccccacccc agtgagcaat agacccccta ccctccccgc   3480
caccgcccag ggccccaccg agaacgacag ccacaacgcc accgagcacc ccgagagcct   3540
gacccagagc gccacccccag gcctgatgac cagcccaacc cagatcgtgc accccagtc    3600 cgccacccct atcaccgtgc aggatacccca ccccagcccc accaacagga gcaagcggaa   3660
cctgaagatg gagatcatcc tgaccctgag ccagggcctg aagaagtact acggcaagat   3720
cctgaggctg ctgcagctga ccctggagga ggacaccgag ggcctgctgg agtggtgcaa   3780
gagaaacctg ggcctggact gcgacgatac cttcttccag aagcggatcg aggagttctt   3840
catcaccggc gagggccact tcaatgaagt gctgcagttc agaaccccg gcaccctgag    3900 caccaccgag tctacccctg ccggcctgcc caccgccgag cccttcaaga gctacttcgc   3960
```

-continued

```
caagggcttc ctgagcatcg acagcggcta ctacagcgcc aagtgctaca gcggcacctc    4020
caacagcgga ctgcagctga tcaacatcac ccggcacagc accagaatcg tggatacccc    4080
tggccccaag atcaccaacc tgaaaaccat caactgcatc aacctgaagg ccagcatctt    4140
caaggagcac cggaagtgg agatcaacgt gctgctgccc caggtggccg tgaatctgag    4200
caactgccac gtggtgatca agagccatgt gtgcgactac agcctggata tcgacggcgc    4260
tgtgagactg ccccacatct accacgaggg cgtgttcatc cctggcacct acaagatcgt    4320
gatcgacaag aagaacaagc tgaacgaccg gtgcaccctg ttcaccgact gcgtgatcaa    4380
gggccgggaa gtgagaaagg gccagagcgt gctgagacag tacaagaccg agatccggat    4440
cggcaaggcc agcaccgggt ccagacgtct tttgagcgag gagcccagcg atgactgcat    4500
cagcaggacc cagctgctga gaaccgagac cgccgagatc cacggcgaca attacggcgg    4560
acccggcgat aagatcacca tctgcaacgg cagcaccatc gtggaccaga gactgggcag    4620
cgagctgggc tgctacacca tcaacagagt gcggagcttc aagctgtgcg agaattccgc    4680
caccggcaag aactgcgaga tcgacagcgt gcccgtgaag tgcagacagg gctactgcct    4740
gaggatcacc caggagggca gaggccacgt gaagctgagc agaggcagcg aagtggtgct    4800
ggatgcctgc gacaccagct gcgagatcat gatccctaag ggcaccggcg atatcctggt    4860
ggactgtagc ggcggacagc agcacttcct gaaggacaac ctgatcgacc tgggctgccc    4920
taagatcccc ctgctgggca agatggctat ctacatctgc cggatgagca accacccaa     4980 gaccaccatg gcctttctgt tctggttcag cttcggctac gtgatcacct gcatcctgtg    5040
caaggccatc ttctacctgc tgatcattgt gggcacctg ggcaagagac tgaagcagta     5100
ccgggagctg aagcccaga cctgcaccat ctgcgagacc acacctgtga acgccatcga     5160
cgccgagatg cacgatttaa attgctccta caacatctgc ccctactgcg ccagcagact    5220
gaccagcgac ggcctggcca gacacgtgat ccagtgcccc aagcggaagg agaaagtgga    5280
ggagaccgag ctgtacctga acctggagag gatcccctgg gttgtgagga agctgctgca    5340
ggtgtccgag agcaccggcg tggccctgaa gagaagcagc tggctgatcg tgctgctggt    5400
gctgttcaca gtgagcctga ccccgtgca gagcgcccct attggccagg caagaccat      5460 cgaggcctac agagccagag agggctacac cagcatctgc ctgttcgtgc tgggcagcat    5520
cctgttcatc gtgtcctgcc tgatgaaggg cctggtggat tctgtgggca acagcttctt    5580
ccctggcctg agcatctgca agacctgcag catcagctcc atcaacggct tcgagatcga    5640
gagccacaag tgctactgct ccctgttctg ctgcccttac tgcagacact gcagcaccga    5700
taaggagatc cacaagctgc acctgtccat ctgtaagaag cggaagaaag tgcagcaatgt   5760 gatgctggcc gtgtgtaagc tgatgtgctt ccgggccacc atggaagtga gcaaccgggc    5820
cctgttcatc cggagcatca tcaacaccac cttcgtgctg tgcatcctga ttctggctgt    5880
gtgcgtggtg tccacctccg ccgtggagat ggagaatctg cctgccggca cctgggagag    5940
agaggaggac ctgaccaact tctgccacca ggagtgccag gtgaccgaga ccgagtgcct    6000
gtgcccctac gaggccctgg tgctgagaaa gccctgttc ctggacagca ccgccaaggg     6060
catgaagaac ctgctgaatt ccacctctct ggagaccagc ctgagcattg aggcccctg     6120 gggcgccatc aacgtgcagt ccacctacaa gcctaccgtg tccaccgcca atatcgccct    6180
gagctggagc agcgtggagc acaggggcaa caagatcctg gtgtccggca gatccgagtc    6240
catcatgaag ctggaggaga ggaccggcat cagctgggac ctgggcgtgg aggacgccag    6300
cgagagcaag ctgctgaccg tgtccgtgat ggacctgagc cagatgtaca gccccgtgtt    6360
```

```
cgagtacctg agcggcgaca gacaagtggg cgagtggccc aaggccacct gcaccggcga   6420
ctgccccgag agatgcggct gcacttctag cacctgcctg cacaaggagt ggccccacag   6480
cagaaactgg agatgcaacc ccacctggtg ctggggagtg ggcaccggct gcacctgctg   6540
tggcctggac gtgaaggacc tgtttaccga ctacatgttc gtgaagtgga aagtggagta   6600
catcaagacc gaggccattg tgtgcgtgga gctgaccagc caggagagac agtgcagcct   6660
gatcgaggcc ggcaccagat tcaacctggg ccccgtgacc atcaccctgt ccgagcccag   6720
aaacatccag cagaagctgc cccctgagat catcacactg caccccagaa tcgaggaggg   6780
cttcttcgac ctgatgcacg tgcagaaagt gctgagcgcc agcacagtgt gcaagctgca   6840
gagctgcacc cacggcgtgc ccggcgacct gcaggtgtac cacatcggca atctgctgaa   6900
gggcgacaaa gtgaacggcc acctgatcca caagatcgag ccccacttca acaccagctg   6960
gatgagctgg gatggctgcg acctggacta ctactgcaac atgggcgact ggcctagctg   7020
cacctacacc ggcgtgaccc agcacaacca cgccagcttc gtgaatctgc tgaacatcga   7080
gaccgactac accaagaact tccacttcca cagcaagaga gtgaccgccc acggcgatac   7140
cccccagctg gacctgaaag ccagacccac ctacggagcc ggcgagatca cagttctggt   7200
ggaagtggcc gatatggagc tgcacaccaa gaagatcgag atcagcggcc tgaagttcgc   7260
cagcctggcc tgtaccggct gctacgcctg cagcagcggc atctcctgca aagtgcggat   7320
ccacgtggac gagcctgacg agctgaccgt gcacgtgaag agcgacgacc ccgacgtggt   7380
ggccgccagc agcagcctga tggccaggaa gctggagttc ggcaccgaca gcaccttcaa   7440
ggccttcagc gccatgccta agacctccct gtgcttctac atcgtggagc gggagcactg   7500
caagagctgt agcgaggagg ataccaagaa gtgcgtgaac accaagctgg aacagcccca   7560
gtccatcctg atcgagcaca agggcaccat catcggcaag cagaacagca cctgtaccgc   7620
caaggccagc tgctggctgg agagcgtgaa gagcttcttc tacgggctga agaatatgct   7680
gagcggcatc ttcggcaacg tgttcatggg catctttctg tttctggccc ccttcatcct   7740
gctgatcctg ttcttcatgt tcggctggcg gatcctgttt tgcttcaagt gctgccggag   7800
aaccagaggc ctgttcaagt accggcacct gaaggacgac gaggagaccg gctaccggag   7860
gatcatcgag aagctgaaca acaagaaggg caagaataag ctgctggacg gcgagagact   7920
ggccgacagg agaatcgccg agctgttcag caccaagacc cacatcggct gatgagcggc   7980
cgcggatcct cgcaatccct aggaggatta ggcaagggct tgagctcacg ctcttgtgag   8040
ggacagaaat acaatcaggg gcagtatatg aatactccat ggagaaaccc agatctacgt   8100
atgatcagcc tcgactgtgc cttctagttg ccagccatct gttgtttgcc cctcccccgt   8160
gccttccttg accctggaag gtgccactcc cactgtcctt tcctaataaa atgaggaaat   8220
tgcatcgcat tgtctgagta ggtgtcattc tattctgggg ggtggggtgg ggcaggacag   8280
caagggggag gattgggaag acaatagcag gcatgctggg gatgcggtgg gctctatggc   8340
ttctgaggcg gaaagaacca gctggggctc gacagctcga ctctagaatt gcttcctcgc   8400
tcactgactc gctgcgctcg gtcgttcggc tgcggcgagc ggtatcagct cactcaaagg   8460
cggtaatacg gttatccaca gaatcagggg ataacgcagg aaagaacatg tgagcaaaag   8520
gccagcaaaa ggccaggaac cgtaaaaagg ccgcgttgct ggcgtttttc cataggctcc   8580
gcccccctga cgagcatcac aaaaatcgac gctcaagtca gaggtggcga aacccgacag   8640
gactataaag ataccaggcg tttccccctg gaagctccct cgtgcgctct cctgttccga   8700
```

-continued

```
ccctgccgct taccggatac ctgtccgcct ttctcccttc gggaagcgtg gcgctttctc    8760
atagctcacg ctgtaggtat ctcagttcgg tgtaggtcgt tcgctccaag ctgggctgtg    8820
tgcacgaacc ccccgttcag cccgaccgct gcgccttatc cggtaactat cgtcttgagt    8880
ccaacccggt aagacacgac ttatcgccac tggcagcagc cactggtaac aggattagca    8940
gagcgaggta tgtaggcggt gctacagagt tcttgaagtg gtggcctaac tacggctaca    9000
ctagaagaac agtatttggt atctgcgctc tgctgaagcc agttaccttc ggaaaaagag    9060
ttggtagctc ttgatccggc aaacaaacca ccgctggtag cggtggtttt tttgtttgca    9120
agcagcagat tacgcgcaga aaaaaaggat ctcaagaaga tcctttgatc ttttctacgg    9180
ggtctgacgc tcagtggaac gaaaactcac gttaagggat tttggtcatg agattatcaa    9240
aaaggatctt cacctagatc cttttaaatt aaaaatgaag ttttaaatca atctaaagta    9300
tatatgagta aacttggtct gacagttacc aatgcttaat cagtgaggca cctatctcag    9360
cgatctgtct atttcgttca tccatagttg cctgactc                           9398
```

<210> SEQ ID NO 3
<211> LENGTH: 5061
<212> TYPE: DNA
<213> ORGANISM: Artificial Sequence
<220> FEATURE:
<223> OTHER INFORMATION: synthesized

<400> SEQUENCE: 3

```
gccaccatgc atatctccct catgtacgcc gtgttctgcc tccaactctg tggcctggga      60
aagactaacg ggcctcacaa cggaactgaa cacaacaaca cccacgtgat gaccacccc     120 gacgactccc agtccccgga gccaccggtg tccaccgccc tgcctgtgac ccccgacccg     180
tccactgtga ccccttccac ccccgcctcc ggcctggagg gcagcggaga agtgtacacc     240
tcctcaccta tcactactaa gggtctgtcc ctgcccgaag cgacctccga gccgcccgcc     300
accacttccg tcgtgaccag ctcggcttcc gacaccgaca gctccactca ggccgcggga     360
gacactccca ccccgaccgt gcggacaagc ctgcccagct cgccgtccac tccttcgact     420
tcccaaggaa ctcactatcc cgtgcgctcg ttgctgtccg tgactagccc taagcctgaa     480 gaaacccca ccccatccaa gtccggaaag gataacctgg ctaccaactc accacacccg     540
gctacttccc gaccgactac ccccccgact accgcgcaga agccgaccga aaacaatagc     600
cacaacacta cggaacagct tgagtccctg acccacctcg ccactctggg ctcaatgatc     660
tcgccgaccc agaccgtgct gcctcagtcg gtgacttcga ttgccatcca ggacattcac     720
aactcgccga cgaaccggtc caagaggaac ctggacatgg agatcatcct gaccctgtcc     780
caaggactga agaaatacta cggcaaaatt cttaagctgc tgcatctgac tctcgaggaa     840
gataccgaag gactgctgga gtggtgcaag cggaacctgg gtctggactg cgatgacacc     900
ttcttccaaa agcggattga ggagttcttc atcacggggg aggggcattt caacgaagtg     960
ctgcagttcc ggaccctggg cactctctcc accaccgaat ccactcacgc cgggtcccca    1020
acagtggaac cattcaagtc atacttcgct aagggattcc tgtccattga ttccggatac    1080
ttcagcgcga gtgctactc gcggacctcg aacagcgggc tccagctgat taacgtgacc    1140
cgccactcaa cgcgcattgc cgataccct ggacctaaga tcaccaacct caagactatc    1200
aactgcatga acctgaaggc ctccgtgttc aaggaacacc gggaggtgga gattaatgtg    1260
ctgctgccgc aagtggccgt gaacctctcg aactgccacg tggccattaa gagccacatt    1320
tgcgattact ccttggatac cgatgggggcg attcggctgc cccaaatcca ccacgaaggc    1380
```

-continued

```
accttcattc cgggaaccta caagatcgtc atcgacaaga agtcgaagct gaacgaccgg   1440
tgtaccctgt tcaccaactg cgtgatcaag ggtagagaag tgcggaaggg acagagcgtg   1500
ctgcggcagt ataagaccga aatccgcatc ggtcgggcat cggcgggaag ccgcagactt   1560
ctgtccgaag aatccggcga cgattgcatt tcgcggaccc agctcctccg cactgaaact   1620
gccgaagtgc acggcgataa ctacggtgga cccggagata agatcacgat ttgtaacgga   1680
tccacggtcg tggaccagag attgggctcc gagctgggtt gctacactat caacagagtc   1740
aggtccttca agctctgcga aaactcagcc acggggaagt cctgcgagat cgactccatc   1800
ccggtcaagt gcaaacaggg ctactgtctg aagatcaccc aggaggggag gggtcacgtc   1860
aagctgagcc ggggatccga agtggtgctg gatgtctgcg attcctcctg tgaagtcatg   1920
atcccgaagg gaaccgggga cattctggtg gactgctcag gaggacagca gcattacctg   1980
aaggacaacc tggtggacct tggatgccca aagattcctc tgctggggaa gatggccatc   2040
tacatctgtc gcatgtcgaa ccaccccaag accactatgg cctttctttt ctggtttagc   2100
ttcggatacg tgatcacttg tatcttgtgc aaggctattt tcttcctgct gatcatcttc   2160
ggcactctgg gcaaaagatt caaacagtac agagaactga aaccacagac ctgtaccatt   2220
tgcgaaacca ctcccgtgaa cgccatcgac gccgagatgc atgatttgaa ctgttcatac   2280
aacatctgcc cctactgcgc gtcgagactc acctcggacg gactcgccag acacgtgacc   2340
cagtgtccga ggcggaagga aaaggtggaa gagactgaac tctatctcaa cctggagaga   2400
attccgtggg tggtcagaaa actgctgcaa gtctctgaaa gcaccggaac cgtgctgaag   2460
agatcgtcct ggctcattgt gctgctcgtg ctgttcaccg tgtcgctgtc gccggtgcag   2520 tccgcccta tcggacacgg gaaaaccatt gaaacttaca gagtgcgcga ggaatacacc   2580
tctatctgcc tgttcgtgct gggatccatt ttgtttatcg tgtccttcct gatgaagggc   2640
ttggtcgacg gggtcggcaa catcttcttc cctggactgt ccgtgtgcaa aacctgttcc   2700
atcggtagca tcaacggctt cgaaattgag tcccacaagt gctactgctc cctgtttttgc   2760 tgcccgtact gccgccactg ttccgcggac ggagagatcc accaattgca tctctcaatc   2820
tgcaagaagc gcaagactgg aagcaacgtg atgctggcag tgtgcaaacg gatgtgtttc   2880
cgggccacca tggaagtctc caacaaggcc ctgtttatcc ggtcgattat caacaccact   2940
tttgtcgtgt gtatcctgat cctcgcggtc tgcgtggtgt caaccagcgc cgtgggagatg   3000 gaaagccttc ccgcggggac ctgggagcgc gaggaggacc tcactaactt ctgccatcaa   3060
gagtgccagg tcaccgagac agagtgcctg tgcccttacg aggctctggt gctgcggcgg   3120
cccctgttcc tggactccat tgtgaaggga atgaagaacc ttctgaactc gacttcgctc   3180
gaaacctccc tcagcattga ggctccttgg ggcgccatca atgtgcagtc cacctacaag   3240
cccaccgtgt ccactgccaa cattgcgctg tcgtggagct ccgtggagca tcggggaaac   3300
aaggtgctcg tgtccggacg ctccgaatct atcatgaagc tcgaggagcg gaccggtatt   3360
tcgtgggacc tgggtgtcga agatgcttcg gagtcaaagc tgcttactgt gtccgtcatg   3420
gatctgtcac aaatgtactc acccgtgttc gaatacctga gcgggggaccg ccaggtcgaa   3480 gagtggccaa aggccacatg caccggagac tgccctgaac gctgtggttg cactagcagc   3540
acttgtctgc acaaggaatg gccgcattcc cgcaactgga ggtgcaaccc gacctggtgc   3600
tggggagtgg aaccggatg cacctgttgc ggactggacg tcaaggacct gttcactgac   3660
tacatgtttg tgaagtggaa ggtcgagtac attaagactg aggccatcgt gtgcgtggag   3720
```

```
ctcacctccc aagaacgcca gtgctccttg atcgaggccg gcacacgctt caatctgggc      3780
tccgtgacga tcaccctgtc tgagcctcgc aacatccagc agaaactgcc gcccgaaatc      3840
atcactcttc atcctaagat cgaggaggga ttcttcgatc tgatgcacgt gcagaaggtc      3900
ctgtcagcat ccaccgtctg caaactgcag tcgtgcaccc atggcgtccc tggcgatctc      3960
caagtgtacc acatcggcaa cttgctgaag ggcgaccgag tgaacggaca ccttatccat      4020
aagattgaac agcacttcaa cacctcctgg atgtcgtggg acggttgcga cctggactac      4080
tactgtaaca tgggagattg gcctagctgc acgtacaccg gtgtcaccca acataaccac      4140
gccagcttcg tcaatctgct gaatatcgaa accgactaca ccaagacctt ccatttccat      4200
tcaaagcgcg tgactgcaca cggagacacc ccgcagcttg acctgaaagc caggcccacc      4260
tacggtgccg gtgaaatcac cgtcctggtg gaagtggcag acatggagct gcacaccaaa      4320
aagatcgaaa tctccggcct gaaattcgcg ggcctgactt gcaccgggtg ctacgcttgc      4380
tcctccggga tctcgtgcaa ggtccgcatt cacgtcgacg agccggatga attgaccgtg      4440
cacgtgaagt ccgacgaccc ggacgtggtc gcagccagcc ccagcctgat ggcccgcaag      4500
cttgaatttg ggaccgatag caccttcaag gccttctcag cgatgcctaa gaccagcctc      4560
tgtttctaca tcgtggaaag agagtattgc aagagctgca gcaaggaaga tacccagaag      4620
tgcgtgaaca ccaaactcga gcagccacaa tccatcctta ttgaacataa ggggactatt      4680
atcggaaaac agaacaacac ttgcaccgcc aaggcctcct gttggctgga atccgtcaag      4740
tctttctttt acggactgaa gaacatgctg ggcggcatct tcggaaacgt gtttattggt      4800
atctttacgt tcctgactcc cttcattctc ctgatcctgt tcttcatgtt tggctggcgc      4860
atcctgttct gctttaagtg ctgcagacgc actaggggac tcttcaagta ccggcacctg      4920
aaggatgatg aggaaaccgg ctacaggaag atcatcgagc ggttgaacaa caagaagggg      4980
aagaatcggc tgctcgacgg cgaacggctc gccgaccgga agatagcaga actcttctca      5040
accaaaaccc acatcggctg a                                                5061
```

```
<210> SEQ ID NO 4
<211> LENGTH: 9280
<212> TYPE: DNA
<213> ORGANISM: Artificial Sequence
<220> FEATURE:
<223> OTHER INFORMATION: Plasmid Construct

<400> SEQUENCE: 4
gggggggggg ggcgctgagg tctgcctcgt gaagaaggtg ttgctgactc ataccaggcc       60
tgaatcgccc catcatccag ccagaaagtg agggagccac ggttgatgag agctttgttg      120
taggtggacc agtggtgat tttgaacttt tgctttgcca cggaacggtc tgcgttgtcg      180
ggaagatgcg tgatctgatc cttcaactca gcaaaagttc gatttattca acaaagccgc      240
cgtcccgtca agtcagcgta atgctctgcc agtgttacaa ccaattaacc aattctgatt      300
agaaaaactc atcgagcatc aaatgaaact gcaatttatt catatcagga ttatcaatac      360
catatttttg aaaaagccgt ttctgtaatg aaggagaaaa ctcaccgagg cagttccata      420
ggatggcaag atcctggtat cggtctgcga ttccgactcg ccaacatca atacaaccta      480 ttaatttccc ctcgtcaaaa ataaggttat caagtgagaa atcaccatga gtgacgactg      540
aatccggtga gaatggcaaa agcttatgca tttctttcca gacttgttca acaggccagc      600
cattacgctc gtcatcaaaa tcactcgcat caaccaaacc gttattcatt cgtgattgcg      660
cctgagcgag acgaaatacg cgatcgctgt taaaaggaca attacaaaca ggaatcgaat      720
```

```
gcaaccggcg caggaacact gccagcgcat caacaatatt ttcacctgaa tcaggatatt      780
cttctaatac ctggaatgct gttttcccgg ggatcgcagt ggtgagtaac catgcatcat      840
caggagtacg gataaaatgc ttgatggtcg gaagaggcat aaattccgtc agccagttta      900
gtctgaccat ctcatctgta acatcattgg caacgctacc tttgccatgt ttcagaaaca      960
actctggcgc atcgggcttc ccatacaatc gatagattgt cgcacctgat tgcccgacat     1020
tatcgcgagc ccatttatac ccatataaat cagcatccat gttggaattt aatcgcggcc     1080
tcgagcaaga cgtttcccgt tgaatatggc tcataacacc ccttgtatta ctgtttatgt     1140
aagcagacag ttttattgtt catgatgata tattttttatc ttgtgcaatg taacatcaga     1200
gattttgaga cacaacgtgg ctttccccccc cccccggca tgcctgcagg tcgacaatat     1260
tggctattgg ccattgcata cgttgtatct atatcataat atgtacattt atattggctc     1320
atgtccaata tgaccgccat gttgacattg attattgact agttattaat agtaatcaat     1380
tacggggtca ttagttcata gcccatatat ggagttccgc gttacataac ttacggtaaa     1440
tggcccgcct ggctgaccgc ccaacgaccc ccgcccattg acgtcaataa tgacgtatgt     1500
tcccatagta acgccaatag ggactttcca ttgacgtcaa tgggtggagt atttacggta     1560
aactgcccac ttggcagtac atcaagtgta tcatatgcca agtccgcccc ctattgacgt     1620
caatgacggt aaatggcccg cctggcatta tgcccagtac atgaccttac gggactttcc     1680
tacttggcag tacatctacg tattagtcat cgctattacc atggtgatgc ggttttggca     1740
gtacaccaat gggcgtggat agcggtttga ctcacgggga tttccaagtc tccacccccat     1800 tgacgtcaat gggagtttgt tttggcacca aaatcaacgg gactttccaa aatgtcgtaa     1860
taaccccgcc ccgttgacgc aaatgggcgg taggcgtgta cggtgggagg tctatataag     1920
cagagctcgt ttagtgaacc gtcagatcgc ctggagacgc catccacgct gttttgacct     1980
ccatagaaga caccgggacc gatccagcct ccgcggccgg gaacggtgca ttggaacgcg     2040
gattccccgt gccaagagtg acgtaagtac cgcctataga ctctataggc acacccctttt    2100 ggctcttatg catgctatac tgttttttggc ttggggccta tacacccccg cttccttatg    2160
ctataggtga tggtatagct tagcctatag gtgtgggtta ttgaccatta ttgaccactc    2220
ccctattggt gacgatactt tccattacta atccataaca tggctctttg ccacaactat    2280
ctctattggc tatatgccaa tactctgtcc ttcagagact gacacggact ctgtattttt    2340
acaggatggg gtcccattta ttatttacaa attcacatat acaacaacgc cgtcccccgt    2400
gcccgcagtt tttattaaac atagcgtggg atctccacgc gaatctcggg tacgtgttcc    2460
ggacatgggc tcttctccgg tagcggcgga gcttccacat ccgagccctg gtcccatgcc    2520
tccagcggct catggtcgct cggcagctcc ttgctcctaa cagtggaggc cagacttagg    2580
cacagcacaa tgcccaccac caccagtgtg ccgcacaagg ccgtggcggt agggtatgtg    2640
tctgaaaatg agctcggaga ttgggctcgc accgctgacg cagatggaag acttaaggca    2700
gcggcagaag aagatgcagg cagctgagtt gttgtattct gataagagtc agaggtaact    2760
cccgttgcgg tgctgttaac ggtggagggc agtgtagtct gagcagtact cgttgctgcc    2820
gcgcgcgcca ccagacataa tagctgacag actaacagac tgttcctttc catgggtctt    2880
ttctgcagtc accgtccaag cttgcggccg cgccaccatg catatctccc tcatgtacgc    2940
cgtgttctgc ctccaactct gtggcctggg aaagactaac gggcctcaca acggaactga    3000
acacaacaac acccacgtga tgaccacccc cgacgactcc cagtccccgg agccaccggt    3060
```

-continued

```
gtccaccgcc ctgcctgtga cccccgaccc gtccactgtg acccccttcca cccccgcctc      3120 cggcctggag ggcagcggag aagtgtacac ctcctcacct atcactacta agggtctgtc      3180
cctgcccgaa gcgacctccg agccgcccgc caccacttcc gtcgtgacca gctcggcttc      3240
cgacaccgac agctccactc aggccgcggg agacactccc accccgaccg tgcggacaag      3300
cctgcccagc tcgccgtcca ctccttcgac ttcccaagga actcactatc ccgtgcgctc      3360
gttgctgtcc gtgactagcc ctaagcctga agaaaccccc accccatcca agtccggaaa      3420
ggataacctg gctaccaact caccacaccc ggctacttcc cgaccgacta cccccccgac      3480
taccgcgcag aagccgaccg aaaacaatag ccacaacact acggaacagc ttgagtccct      3540
gacccacctc gccactctgg gctcaatgat ctcgccgacc cagaccgtgc tgcctcagtc      3600
ggtgacttcg attgccatcc aggacattca caactcgccg acgaaccggt ccaagaggaa      3660
cctggacatg gagatcatcc tgaccctgtc ccaaggactg aagaaatact acggcaaaat      3720
tcttaagctg ctgcatctga ctctcgagga agataccgaa ggactgctgg agtggtgcaa      3780
gcggaacctg ggtctggact gcgatgacac cttcttccaa aagcggattg aggagttctt      3840
catcaccggg gagggggcatt tcaacgaagt gctgcagttc cggaccctgg gcactctctc      3900
caccaccgaa tccactcacg ccgggtcccc aacagtggaa ccattcaagt catacttcgc      3960
taagggattc ctgtccattg attccggata cttcagcgcg aagtgctact cgcggacctc      4020
gaacagcggg ctccagctga ttaacgtgac ccgccactca acgcgcattg ccgatacccc      4080
tggacctaag atcaccaacc tcaagactat caactgcatg aacctgaagg cctccgtgtt      4140
caaggaacac cgggaggtgg agattaatgt gctgctgccg caagtggccg tgaacctctc      4200
gaactgccac gtggccatta agagccacat ttgcgattac tccttggata ccgatggggc      4260
gattcggctg ccccaaatcc accacgaagg caccttcatt ccgggaacct acaagatcgt      4320
catcgacaag aagtcgaagc tgaacgaccg gtgtaccctg ttcaccaact gcgtgatcaa      4380
gggtagagaa gtgcggaagg gacagagcgt gctgcggcag tataagaccg aaatccgcat      4440
cggtcgggca tcggcgggaa gccgcagact tctgtccgaa gaatccggcg acgattgcat      4500
ttcgcggacc cagctcctcc gcactgaaac tgccgaagtg cacggcgata actacggtgg      4560
acccggagat aagatcacga tttgtaacgg atccacggtc gtggaccaga gattgggctc      4620
cgagctgggt tgctacacta tcaacagagt caggtccttc aagctctgcg aaaactcagc      4680
cacggggaag tcctgcgaga tcgactccat cccggtcaag tgcaaacagg gctactgtct      4740
gaagatcacc caggaggga ggggtcacgt caagctgagc cggggatccg aagtggtgct      4800
ggatgtctgc gattcctcct gtgaagtcat gatcccgaag ggaaccgggg acattctggt      4860
ggactgctca ggaggacagc agcattacct gaaggacaac ctggtggacc ttggatgccc      4920
aaagattcct ctgctgggga agatggccat ctacatctgt cgcatgtcga accaccccaa      4980
gaccactatg gcctttcttt tctggtttag cttcggatac gtgatcactt gtatcttgtg      5040
caaggctatt ttcttcctgc tgatcatctt cggcactctg ggcaaaagat tcaaacagta      5100
cagagaactg aaaaccacaga cctgtaccat ttgcgaaacc actcccgtga acgccatcga      5160
cgccgagatg catgatttga actgttcata caacatctgc ccctactgcg cgtcgagact      5220
cacctcggac ggactcgcca gacacgtgac ccagtgtccg aggcggaagg aaaaggtgga      5280
agagactgaa ctctatctca acctggagag aattccgtgg gtggtcagaa aactgctgca      5340
agtctctgaa agcaccggaa ccgtgctgaa gagatcgtcc tggctcattg tgctgctcgt      5400
gctgttcacc gtgtcgctgt cgccggtgca gtccgcccct atcggacacg ggaaaaccat      5460
```

-continued

```
tgaaacttac agagtgcgcg aggaatacac ctctatctgc ctgttcgtgc tgggatccat    5520
tttgtttatc gtgtccttcc tgatgaaggg cttggtcgac ggggtcggca acatcttctt    5580
ccctggactg tccgtgtgca aaacctgttc catcggtagc atcaacggct tcgaaattga    5640
gtcccacaag tgctactgct ccctgttttg ctgcccgtac tgccgccact gttccgcgga    5700
cggagagatc caccaattgc atctctcaat ctgcaagaag cgcaagactg gaagcaacgt    5760
gatgctggca gtgtgcaaac ggatgtgttt ccgggccacc atggaagtct ccaacaaggc    5820
cctgtttatc cggtcgatta tcaacaccac ttttgtcgtg tgtatcctga tcctcgcggt    5880
ctgcgtggtg tcaaccagcg ccgtggagat ggaaagcctt cccgcgggga cctgggagcg    5940
cgaggaggac ctcactaact tctgccatca agagtgccag gtcaccgaga cagagtgcct    6000
gtgcccttac gaggctctgg tgctgcggcg gcccctgttc ctggactcca ttgtgaaggg    6060
aatgaagaac cttctgaact cgacttcgct cgaaacctcc ctcagcattg aggctccttg    6120
gggcgccatc aatgtgcagt ccacctacaa gcccaccgtg tccactgcca acattgcgct    6180
gtcgtggagc tccgtggagc atcggggaaa caaggtgctc gtgtccggac gctccgaatc    6240
tatcatgaag ctcgaggagc ggaccggtat ttcgtgggac ctgggtgtcg aagatgcttc    6300
ggagtcaaag ctgcttactg tgtccgtcat ggatctgtca caaatgtact cacccgtgtt    6360
cgaatacctg agcgggggacc gccaggtcga gagtggcca aaggccacat gcaccggaga    6420
ctgccctgaa cgctgtggtt gcactagcag cacttgtctg cacaaggaat ggccgcattc    6480
ccgcaactgg aggtgcaacc cgacctggtg ctggggagtg ggaaccggat gcacctgttg    6540
cggactggac gtcaaggacc tgttcactga ctacatgttt gtgaagtgga aggtcgagta    6600
cattaagact gaggccatcg tgtgcgtgga gctcacctcc caagaacgcc agtgctcctt    6660
gatcgaggcc ggcacacgct tcaatctggg ctccgtgacg atcaccctgt ctgagcctcg    6720
caacatccag cagaaactgc cgcccgaaat catcactctt catcctaaga tcgaggaggg    6780
attcttcgat ctgatgcacg tgcagaaggt cctgtcagca tccaccgtct gcaaactgca    6840
gtcgtgcacc catggcgtcc ctggcgatct ccaagtgtac cacatcggca acttgctgaa    6900
gggcgaccga gtgaacggac accttatcca taagattgaa cagcacttca acacctcctg    6960
gatgtcgtgg gacggttgcg acctggacta ctactgtaac atgggagatt ggcctagctg    7020
cacgtacacc ggtgtgcaccc aacataacca cgccagcttc gtcaatctgc tgaatatcga    7080
aaccgactac accaagacct tccatttcca ttcaaagcgc gtgactgcac acggagacac    7140
cccgcagctt gacctgaaag ccaggcccac ctacggtgcc ggtgaaatca ccgtcctggt    7200
ggaagtggca gacatggagc tgcacaccaa aaagatcgaa atctccggcc tgaaattcgc    7260
gggcctgact tgcaccgggt gctacgcttg ctcctccggg atctcgtgca aggtccgcat    7320
tcacgtcgac gagccggatg aattgaccgt gcacgtgaag tccgacgacc ggacgtggt    7380 cgcagccagc tccagcctga tggcccgcaa gcttgaattt gggaccgata gcaccttcaa    7440
ggccttctca gcgatgccta agaccagcct ctgtttctac atcgtggaaa gagagtattg    7500
caagagctgc agcaaggaag atacccagaa gtgcgtgaac accaaactcg agcagccaca    7560
atccatcctt attgaacata aggggactat tatcggaaaa cagaacaaca cttgcaccgc    7620
caaggcctcc tgttggctgg aatccgtcaa gtctttcttt tacggactga agaacatgct    7680
gggcggcatc ttcggaaacg tgtttattgg tatctttacg ttcctgactc ccttcattct    7740
cctgatcctg ttcttcatgt ttggctggcg catcctgttc tgctttaagt gctgcagacg    7800
```

-continued

```
cactagggga ctcttcaagt accggcacct gaaggatgat gaggaaaccg gctacaggaa   7860
gatcatcgag cggttgaaca acaagaaggg gaagaatcgg ctgctcgacg gcgaacggct   7920
cgccgaccgg aagatagcag aactcttctc aaccaaaacc cacatcggct gaagatctac   7980
gtatgatcag cctcgactgt gccttctagt tgccagccat ctgttgtttg cccctccccc   8040
gtgccttcct tgaccctgga aggtgccact cccactgtcc tttcctaata aaatgaggaa   8100
attgcatcgc attgtctgag taggtgtcat tctattctgg ggggtggggt ggggcaggac   8160
agcaaggggg aggattggga agacaatagc aggcatgctg gggatgcggt gggctctatg   8220
gcttctgagg cggaaagaac cagctggggc tcgacagctc gactctagaa ttgcttcctc   8280
gctcactgac tcgctgcgct cggtcgttcg gctgcggcga gcggtatcag ctcactcaaa   8340
ggcggtaata cggttatcca cagaatcagg ggataacgca ggaaagaaca tgtgagcaaa   8400
aggccagcaa aaggccagga accgtaaaaa ggccgcgttg ctggcgtttt tccataggct   8460
ccgcccccct gacgagcatc acaaaaatcg acgctcaagt cagaggtggc gaaacccgac   8520
aggactataa agataccagg cgtttccccc tggaagctcc ctcgtgcgct ctcctgttcc   8580
gaccctgccg cttaccggat acctgtccgc ctttctccct tcgggaagcg tggcgctttc   8640
tcatagctca cgctgtaggt atctcagttc ggtgtaggtc gttcgctcca agctgggctg   8700
tgtgcacgaa ccccccgttc agcccgaccg ctgcgcctta tccggtaact atcgtcttga   8760
gtccaacccg gtaagacacg acttatcgcc actggcagca gccactggta acaggattag   8820
cagagcgagg tatgtaggcg gtgctacaga gttcttgaag tggtggccta actacggcta   8880
cactagaaga acagtatttg gtatctgcgc tctgctgaag ccagttacct cggaaaaag   8940 agttggtagc tcttgatccg gcaaacaaac caccgctggt agcggtggtt tttttgtttg   9000
caagcagcag attacgcgca gaaaaaaagg atctcaagaa gatcctttga tcttttctac   9060
ggggtctgac gctcagtgga acgaaaactc acgttaaggg attttggtca tgagattatc   9120
aaaaaggatc ttcacctaga tccttttaaa ttaaaaatga agttttaaat caatctaaag   9180
tatatatgag taaacttggt ctgacagtta ccaatgctta atcagtgagg cacctatctc   9240
agcgatctgt ctatttcgtt catccatagt tgcctgactc                          9280
```

CRIMEAN-CONGO HEMORRHAGIC FEVER VIRUS M-SEGMENT NUCLEIC ACID VACCINE AND METHODS OF USE AND PRODUCTION

STATEMENT REGARDING FEDERALLY SPONSORED RESEARCH

This invention was made with government support under proposal number T0210-19-RD awarded by the United States Army Medical Research and Development Command. The U.S. government has certain rights in the invention.

SEQUENCE LISTING

The instant application contains a Sequence Listing, which has been submitted electronically in ASCII format and is hereby incorporated by reference in its entirety. Said ASCII copy, created on Dec. 5, 2023, is named "RIID_20_18_ST25.txt" and is 38,354 bytes in size.

BACKGROUND

Crimean-Congo hemorrhagic fever virus (CCHFV) is a tick-borne member of the family Nairoviridae in the order Bunyavirales with the widest geographical distribution. CCHFV infection in humans causes a severe and often fatal disease with a mortality rate ranging from 3-60%[1]. CCHFV has a tripartite, negative sense RNA genome comprised of a small (S), medium (M), and large (L) segment. The S segment encodes the nucleocapsid (N) protein, the M-segment encodes the glycoprotein precursor complex (GPC), containing two glycoproteins ($G_N$ and $G_C$) as well as several non-structural proteins (mucin-like domain, GP38, GP160, GP85, and $NS_M$), and the L segment encodes the RNA-dependent RNA polymerase[2]. Depending on the algorithm used in analysis, CCHFV is the most genetically diverse of the arboviruses with 6-7 virus clades, and with nucleotide divergence of 20% among the S-segments, 22% among the L-segments, and the largest divergence of 31% among the M segments[1]. Although the M-segment is the most diverse, the majority of the variation is in the N-terminal non-structural domains. The optimal CCHF vaccine will account for this high genetic diversity and confer broad protection against divergent strains. As of 2015, CCHF is designated a top ten priority emerging infectious disease by the World Health Organization[3, 4]. This classification has led to increased focus on the development of a protective CCHF vaccine.

CCHF vaccine efforts are hindered by a lack of knowledge regarding the necessary immune response(s) required for protection against disease. While robust levels of IgM and IgG have been identified as clinical indicators of survival[5], the correlates of protection remain to be established experimentally[6]. In mouse models, antibody responses following vaccination appear beneficial; however, they do not necessarily predict survival[6-8] at least because a correlation between the humoral response and survival has not been established[7-10]. Furthermore, adoptive transfer of T cells or sera from vaccinated mice to naïve recipients does not significantly improve survival following CCHFV challenge, but a combination of anti-CCHFV T cells and antibodies offers some protection[11]. These results suggest that both arms of the adaptive immune response are critical for controlling CCHFV infection and that any efficacious vaccine will need to elicit antigen-specific T cells and antibodies.

Most CCHF vaccines focus on the M-segment, as the glycoproteins are accessible on the virion surface and are the target of neutralizing and non-neutralizing antibodies. Multiple vaccine platforms containing either the full-length M-segment or $G_N$/$G_C$ have been described[7, 9, 12]. Notably, DNA vaccination has proven capable of eliciting protective anti-CCHFV immune responses, possibly due to the ability of DNA vaccines to generate both humoral and cellular immunity. A triple plasmid formulation consisting of individual plasmids expressing $G_N$, $G_C$, and N yielded high-level antibody responses and conferred protection against CCHFV challenge[10]. N vaccination alone can offer significant protection[13, 14]. But, the protective response elicited by each and every vaccine component was not fully characterized.

The majority of CCHF vaccines have been tested against homologous challenge. Canakoglu et al. tested a formalin-inactivated vaccine based on the Turkey-Kelkit06 strain[15], but the majority of CCHF vaccines are designed using the laboratory-adapted strain, CCHFV-IbAr 10200. Two notable exceptions of heterologous challenge studies are a virus-like replicon particle (VRP) vaccine expressing the GPC of the Oman-1998 strain tested against CCHFV-IbAr 10200, and a replication-competent recombinant vesicular stomatitis virus (rVSV) expressing the CCHFV-IbAr 10200 GPC against the Turkey 200406546 strain[12,16]. It remains to be investigated whether CCHFV-IbAr 10200-based vaccines can provide cross-protection against challenge with other clinically relevant CCHFV strains. Additionally, the divergent epitopes that may influence cross-protection require examination.

In this report, we further expanded on efforts to produce a simplified, efficacious CCHFV M-segment vaccine. We tested a vaccine dose in an effort to improve the immune response and provide complete protection against lethal CCHFV challenge with the homologous strain, as well as provide cross-protection against a divergent CCHFV strain. We also designed and tested a DNA vaccine expressing the M-segment of the clinically relevant CCHFV-Afg09-2990 strain. Finally, we investigated the role of the non-structural M-segment protein, GP38, in CCHF vaccine efficacy. To our knowledge, this is the first study to report on heterologous protection of a DNA vaccine containing only a single plasmid. We also believe it to be the first report to identify a specific non-structural M-segment region that influences the immune response of CCHF vaccines.

BRIEF DESCRIPTION OF THE DRAWINGS

The detailed description of preferred embodiments of the invention will be better understood when read in conjunction with the appended drawings. For the purpose of illustrating the invention, the drawings show certain, but not all, preferred embodiments. It should be understood that embodiments of the invention are not limited to the precise arrangements and instrumentalities of those shown in the drawings.

FIG. 2A. CCHFV-IbAr 10200-specific antibody responses were analyzed 21 days post third vaccination for ELISA endpoint titers. Mice that succumbed to challenge are highlighted red. FIG. 2B. Temporal anti-CCHFV-IbAr 10200 IgG responses in vaccinated mice. The arrows indicate DNA vaccination time points. Data are the group mean averages+/−SD. ***$p<0.001$. The endpoint titer p value was determined by Student's t test with a 95% confidence interval.

FIGS. 3A, 3B, 3C, and 3D: Anti-M cellular immune responses are specific to defined regions. Groups of 9 female C57BL/6 mice were vaccinated with 50 μg CCHFV-$M_{10200}$ (8.5 μmoles) or empty vector on days 0, 21, and 42 by IM-EP, and then euthanized on day 49 for splenocyte T cell analysis. Splenocytes from individual mice were re-stimulated with pooled peptides derived from the CCHFV-IbAr 10200 M-segment. Anti-CCHFV-M specific IFN-$\gamma^+$ (FIG. 3A) and IL-$2^+$ T cells (FIG. 3B) were quantified by ELISPOT. The corresponding region of the peptide pools to the M-segment are shown below each graph. Percentage of IFN-$\gamma^+$ (FIG. 3C) and IL-$2^+$ (FIG. 3D) T cells responding to each peptide pool. Data are the group mean averages+/−SD. *$p<0.05$; $p<0.01$; *$p<0.001$; ***$p<0.0001$. p values were determined by two-way ANOVA with Sidak's multiple comparison test with a 95% confidence interval.

FIGS. 4A, 4B, 4C, and 4D: CCHFV-IbAr 10200-specific T cells are not cross-reactive with the CCHFV-Afg09-2990 MLD or GP38. Groups of 10 female C57BL/6 mice were vaccinated with 50 μg CCHFV-$M_{10200}$ (8.5 μmoles) or empty vector on days 0, 21, and 42 by IM-EP, and then euthanized on day 49 for splenocyte T cell analysis. Splenocytes from individual mice were re-stimulated with pooled peptides derived from the CCHFV strain Afg09-2990 M-segment. Anti-CCHFV-Afg09-2990 specific IFN-$\gamma^+$ (FIG. 4A) and IL-$2^+$ T cells (FIG. 4B) were quantified by ELISPOT. The corresponding region of the peptide pools to the M-segment are shown below each graph. Percentage of IFN-$\gamma^+$ (FIG. 4C) and IL-$2^+$ (FIG. 4D) T cells responding to each peptide pool. Data are the group mean averages+/−SD. *$p<0.001$; *$p<0.0001$. p values were determined by two-way ANOVA with Sidak's multiple comparison test with a 95% confidence interval.

FIG. 5A. Sera antibody responses were analyzed 21 days post third vaccination for anti-CCHFV-IbAr 10200 or anti-CCHFV-Afg09-2990 endpoint titers by ELISA. Mice that succumbed to viral challenge are shown in red. FIG. 5B. Temporal anti-CCHFV IgG responses in vaccinated mice. The arrows indicate DNA vaccination time points. Data are the group mean averages+/−SD. ***$p<0.0001$. p values were determined by one-way ANOVA with Tukey's post hoc test with a 95% confidence interval.

FIGS. 8A, 8B, 8C, and 8D: CCHFV-$M_{Afg09}$ DNA vaccination is completely protective against homologous challenge. Groups of 10 female C57BL/6 mice were vaccinated with 50 μg CCHFV-$M_{Afg09}$ (8.5 μmoles) or empty vector on days 0, 21, and 42 by IM-EP. FIG. 8A. Sera antibody responses were analyzed 21 days post third vaccination for anti-CCHFV-Afg09-2990 endpoint titers by ELISA. Mice that succumbed to viral challenge are shown in red. FIG. 8B Temporal anti-CCHFV-Afg09-2990 IgG responses in vaccinated mice. The arrows indicate DNA vaccination time points. Group survival (FIG. 8C) and weight change (FIG. 8D) following CCHFV challenge with 100 PFU by the IP route with CCHFV-Afg09-2990. Vaccinated C57BL/6 mice were transiently immunosuppressed prior to challenge. Data are the group mean averages+/−SD. ***$p<0.0001$. The endpoint titer p value was determined by Student's t test with a 95% confidence interval. The p value for percent survival was determined by log rank test with a 95% confidence interval.

FIG. 9A. Sera antibody responses were analyzed 21 days post third vaccination for anti-CCHFV endpoint titers by ELISA. Mice that succumbed to viral challenge are shown in red. FIG. 9B. Anti-CCHFV-IbAr 10200 GP38 IgG responses in vaccinated mice. Group survival (FIG. 9C) and weight change (FIG. 9D) following challenge with 100 PFU by the IP route with CCHFV-IbAr 10200, Vaccinated C57BL/6 mice were transiently immunosuppressed prior to challenge. Comparison of the anti-CCHFV-IbAr 10200 GP38 antibody response from CCHFV-$M_{10200}$ and CCHFV-$M_{Afg09}$ vaccinated mice (FIG. 9E). Data are the group mean averages+/−SD. *$p<0.05$; $p<0.01$; *$p<0.001$; ***$p<0.0001$. Endpoint titer p values were determined by one-way ANOVA with Tukey's post hoc test with a 95% confidence interval. p values for percent survival were determined by log rank test with a 95% confidence interval.

FIG. 12: Nucleotide sequence of the codon-optimized sequence of the M-segment of CCHFV strain IbAr 10200 (SEQ ID NO: 1).

FIG. 13: Nucleotide sequence of the codon-optimized sequence of the M-segment of CCHFV strain IbAr 10200 inserted into pWRG7077 (SEQ ID NO: 2).

FIG. 14: Nucleotide sequence of the codon-optimized sequence of the M-segment of CCHFV strain Afg09-2990 (SEQ ID NO: 3).

FIG. 15: Nucleotide sequence of the codon-optimized sequence of the M-segment of CCHFV strain Afg09-2990 inserted into pWRG7077 (SEQ ID NO: 4).

DETAILED DESCRIPTION

Definitions

Figures 1A, 1B:
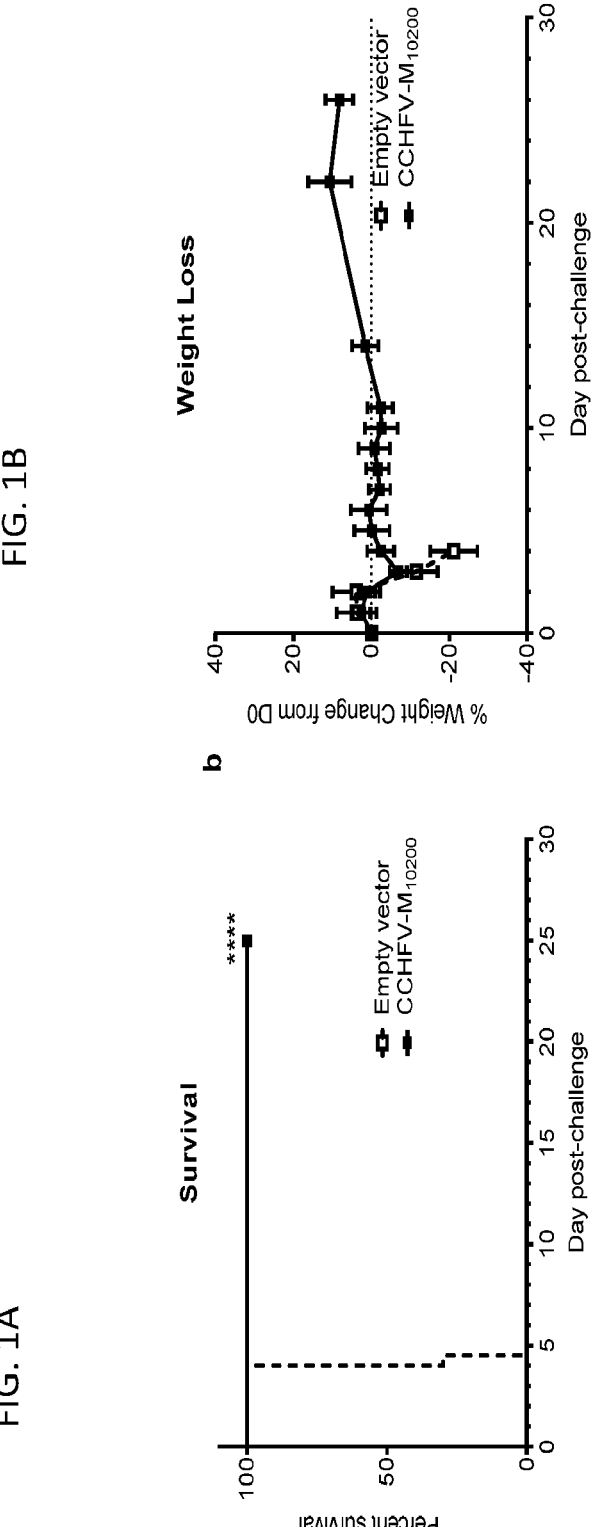
FIGS. 1A and 1B: CCHFV-$M_{100200}$ DNA vaccination completely protects against homologous challenge. Groups of 10 C57BL/6 female mice were vaccinated with 50 g CCHFV-$M_{10200}$ (8.5 µmoles) or empty vector on days 0, 21, and 42 by IM-EP. Group survival (FIG. 1A) and weight change (FIG. 1B) of CCHFV-$M_{10200}$ vaccinated mice following CCHFV challenge with 100 PFU by the IP route with the homologous CCHFV-IbAr 10200 strain. Vaccinated C57BL/6 mice were transiently immunosuppressed prior to challenge. ****p<0.0001. The percent survival p value was determined by a log rank test.

The preferred materials and methods are described herein; any methods and materials similar or equivalent to those described herein can be used in the practice of or testing of the invention. Unless defined otherwise, all technical and scientific terms herein have the same meaning as commonly understood by one of ordinary skill in the art to which the invention pertains. In describing and claiming the present invention, the following terminology will be used. It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element. Unless otherwise indicated, "or" encompasses "and." To illustrate, "A, B, or C" means A alone, B alone, C alone, the combination of A and B, the combination of A and C, the combination of B and C, and the combination of A, B, and C, unless otherwise illustrated.

"About" as used herein when referring to a measurable value such as an amount, a temporal duration, a quantum of measurement, and the like, is meant to encompass variations of .+−.20% or .+−.10%, more preferably .+−.5%, even more preferably .+−.1%, and still more preferably .+−.0.1% from the specified value, as such variations are appropriate to perform the disclosed methods.

The terms "administering" or "administration" of an agent, drug, or peptide to a subject refers to any route of introducing or delivering to a subject a compound to perform its intended function. The administering or administration can be carried out by any suitable route, including orally, intranasally, parenterally (intravenously, intramuscularly, intraperitoneally, or subcutaneously), rectally, or topically. Administering or administration includes self-administration and the administration by another.

The terms "co-administration", "co-administered" or "co-administering" as used herein refer to the administration of a substance before, concurrently, or after the administration of another substance such that the biological effects of either substance synergistically overlap.

The term "antigen" or "Ag", unless otherwise indicated, is defined as a molecule that provokes an immune response.

This immune response may involve either antibody production, or the activation of specific immunologically-competent cells (e.g. through T cell receptor activation), or both. Any macromolecule, including virtually all proteins, peptides, carbohydrate, nucleotide, viruses, or fragments thereof can serve as an antigen. Furthermore, antigens can be generated from recombinant or genomic DNA or from RNA or DNA from a virus. Any DNA or RNA, which comprises a nucleotide sequences or a partial nucleotide sequence encoding a protein that elicits an immune response therefore encodes an "antigen" as that term is used herein. An antigen need not be encoded solely by a full-length nucleotide sequence (e.g. a full gene). In certain embodiments, the use of partial nucleotide sequences of more than one gene or transcript thereof and that these nucleotide sequences are arranged in various combinations to elicit the desired immune response. An antigen need not be encoded by a "gene" at all, and may comprise, for example, sugars or non-coding nucleic acids, alone or in combination with a protein or peptide. An antigen can be generated, synthesized, or originate from a biological sample. Such a biological sample can include, but is not limited to a tissue sample, a cell, or a biological fluid. For example, a biological sample can comprise a producing cell line, a virus, and culture media, wherein the producing cell line produces the virus, and wherein the virus may or may not be released into the culture media.

The term "codon optimization" or "codon optimized" refers to the discover that the frequency of occurrence of synonymous codons (i.e., codons that code for the same amino acid) in coding DNA is biased within a species, and that depending upon the species, two differing nucleic acids that code for the same protein can result in the differential expression of the mRNA or the protein depending upon the particular codons "preferred" in that species. The mRNA produced from the modified nucleic acid that contains the "preferred codons" for a particular species might be expressed more efficiently or at higher levels in that species or the protein expressed therefrom might be expressed more efficiency or at higher levels in that species and that modified nucleic acid is thereby "codon optimized" or has undergone "codon optimization" when compared to the other nucleic acid, which might be naturally occurring or not codon optimized. Depending upon the comparison, further codon optimization may be obtained over a sequence which is not fully codon optimized, but in absolute terms, both are "codon optimized." Rather, further codon optimization may be referred to in relative terms.

The term "compound", unless otherwise indicated, refers to any specific chemical compound, including an antigen, adjuvant, and/or drug. "Compound" can include tautomers, regioisomers, geometric isomers, optical isomers, pharmaceutically acceptable salts, and specific enantiomers or enantiomerically enriched mixtures of any specific chemical compound, including those that naturally occur from the specific chemical compound being placed into a solution.

The term "antigenic composition" refers to a composition which contains one or more antigens. Antigenic compositions are used to generate an immunogenic response in a subject upon administration, introduction, or exposure.

The term "immune response", unless otherwise indicated, refers to a humoral immune response and/or cell-mediated immune response leading to the activation or proliferation of B- and/or T-lymphocytes and/or and antigen presenting cells. "Adaptive immune response" is also known as and used interchangeably with "acquired immune response" and both, unless otherwise indicated, refers to a humoral immune response and/or cell-mediated immune response leading to activation and proliferation of B- and/or T-lymphocytes and, though not necessarily, activation and proliferation of antigen presenting cells, but can include it. "Innate immune response" refers to a non-B and/or T-lymphocyte mediated immune response and can include an In some instances, however, the immune responses may be of low intensity and become detectable only when using at least one composition disclosed herein, including a coronavirus antigen.

"Immunogenic" refers to an agent used to stimulate the immune system of a living organism, so that one or more functions of the immune system are increased and directed towards the immunogenic agent. An "immunogenic polypeptide", "immunogenic protein", "immunogenic peptide" is a polypeptide, protein, or peptide that elicits a cell-mediated and/or humoral immune response, whether alone or linked to a carrier in the presence or absence of an adjuvant. Preferably, antigen presenting cells may be activated.

In some embodiments, the composition further comprises a pharmaceutically acceptable substance, such as a pharmaceutically acceptable carrier, additive, or excipient. The term "pharmaceutically acceptable", unless otherwise specified, when used within the context of a carrier, additive, or excipient, is one that is not unacceptably toxic to the subject to which it is administered. Pharmaceutically acceptable carriers, additives, or excipients can comprise: (1) fillers or extenders including, but not limited to, as starches, lactose, sucrose, glucose, mannitol, and/or silicic acid; (2) binders including, but not limited to, carboxymethylcellulose, alginates, gelatin, polyvinyl pyrrolidone, sucrose, and/or acacia; (3) humectants including, but not limited to, glycerol; (4) disintegrating agents including, but not limited to, agar-agar, calcium carbonate, potato or tapioca starch, alginic acid, certain silicates, and sodium carbonate; (5) solution retarding agents, such as paraffin; (6) absorption accelerators including, but not limited to, quaternary ammonium compounds; (7) wetting agents including, but not limited to, cetyl alcohol and glycerol monostearate; (8) absorbents including, but not limited to, kaolin and bentonite clay; (9) lubricants including, but not limited to, talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. By way of example, a pharmaceutically acceptable carrier, additive, or excipient can include sodium citrate or calcium carbonate.

The term "promoter" as used herein is defined as a DNA sequence recognized by the synthetic machinery of the cell, or introduced synthetic machinery, required to initiate the specific transcription of a polynucleotide sequence. As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner. A "constitutive" promoter is a nucleotide sequence which, when operably linked with a polynucleotide which encodes or specifies a gene product, causes the gene product to be produced in a cell under most or all physiological conditions of the cell. An "inducible" promoter is a nucleotide sequence which, when operably linked with a polynucleotide which encodes or specifies a gene product, causes the gene product to be produced in a cell substantially only when an inducer which corresponds to the promoter is present in the cell. A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The term "prophylactic", "providing an immunogenic response", "vaccinating" is used to describe the use of a compound described herein which reduces the likelihood of an occurrence of a condition or disease state and/or reducing the number of symptoms or likelihood of developing a symptom in a patient or subject. In this regard, "prevent" or "prophylactic" should not be understood to absolutely prevent the disease in the entire population, as it is epidemiologically impossible to attribute "prevent" to mean "absolute prevention." The term "reducing the likelihood" refers to the fact that in a given population of subjects, the embodiments herein may be used to reduce the likelihood of an occurrence or recurrence of disease or to reduce the likelihood of one or more symptoms in one or more subjects within that population of all subjects, rather than prevent, in all subjects, the occurrence or recurrence of a disease state or each symptom or each and every symptom.

When the immune response to an antigen, by itself, is weak, short-lived, or otherwise insufficient, the immune response to the antigen can be boosted by administering an adjuvant separately or in combination with the antigen and/or nucleic acids encoding the antigen. In some embodiments, the administration of the adjuvant boosts the immune response. In some embodiments, the administration of the adjuvant boosts the adaptive immune response. In some embodiments, the administration of the adjuvant boosts the humoral and/or cell-mediated immune response. In some embodiments, the immune response, including an adaptive immune response, and further including a humoral and/or cell-mediate immune response, is boosted by being greater when the method comprises administering an antigen and adjuvant or the composition comprises an antigen and an antigen than the immune response obtained from exposure to the antigen alone. In some embodiments, said greater immune response occurs the adjuvant and antigen are administered in combination, or the formulation provides exposure to the antigen and adjuvant simultaneously. In some embodiments, said greater immune response occurs when the adjuvant and antigen are administered separately, or the formulation or compositions provides temporally and/or spatially separate exposure to the antigen and adjuvant.

In some embodiments, separate spatial exposure to the antigen and adjuvant is the exposure of one tissue to the adjuvant and another tissue to the antigen. In some embodiments, separate spatial and or temporal exposure to the antigen and adjuvant is achieved by formulating the composition such that the antigen and adjuvant are in separate layers of the formulation, preferably wherein they are separated by a timed-release layer or in separate parts of the formulation, each differing in its temporal or physiological (i.e. pH) release characteristics.

"Subject" or "patient" means an animal to whom compositions is administered, treated, or prophylactically treated and/or to whom methods of administration, treatment, and/or prophylactic treatment are directed. In certain embodiments, a subject is a mammal, including human, a domesticated animal, including a camel, and laboratory test animal, including a mouse or a non-human primate, such as a macaque. In certain embodiments, a subject is further preferably a human, a camel, a macaque, or a mouse.

Within the context of an amount, "effective"—as in "effective amount"—describes an amount of a compound, composition, or component, which is used to produce or effect an intended result, whether that result relates to eliciting an immunogenic response, elucidating a specific immune response to the administered antigen or nucleic acid encoding the antigen, or whether that result relates to the treatment or prevention/prophylaxis of a disorder or condition associated with the present invention or alternatively, is used to produce another compound, agent, or composition (i.e. an antibody). This term subsumes all other effective amount or effective concentration terms which are otherwise described herein.

Effective amount also encompasses an amount sufficient to be biologically active for a sufficient duration to produce or effect the intended result, such as an immunogenic response, in the intended or target tissue. A compound is subject to pharmacokinetics (administration, e.g. adherence and route; bioavailability, e.g. the production of an antigen from a nucleic acid, absorption and first pass metabolism and activation including conversion from "pro" forms; and distribution, e.g. diffusion and transport; and clearance, e.g. metabolism and clearance) and pharmacodynamics (concentration at target, affinity to target, molecular effects, physiological effects), and accordingly the "effective amount" accounts for the effects of pharmacodynamics at the target tissue and pharmacokinetics of the modality of administration to the target tissue in achieving the intended result.

Methods and Compositions

In some embodiments, a method of increasing the likelihood of survival or decreasing the likelihood or severity of at least one symptom from a Congo-Crimean Hemorrhagic Fever Virus (CCHFV) in a subject in need thereof is provided. In some embodiments, the method comprises administering a vaccine comprising a vector comprising a promoter and 8.5 µmoles or more of the nucleic acid of SEQ ID NO: 1 or 3 or 0.385 µmoles or more of the nucleic acid of SEQ ID NO: 1 or 3 per gram body weight of the subject. In some embodiments, the method comprises administering an effective amount of a vaccine comprising a vector comprising a promoter and the nucleic acid of SEQ ID NO: 1 or 3. In some embodiments, the nucleic acid of SEQ ID NO: 1 or 3 is operably linked to the promoter. In some embodiments, the administering provides at least a 60%, 70%, 80%, 90%, 95%, 96%, 97%, 98%, 99%, 99.8%, 99.9%, or 100% likelihood of survival in the subject five days after exposure to the CCHFV. In some embodiments, the administering reduces the likelihood of a greater than 10% weight loss in the subject after exposure to the CCHFV.

In some embodiments, the vaccine is administered orally, subcutaneously, intramuscularly, intradermally, or intranasally.

In some embodiments, the CCHFV is not IbAr 10200, In some embodiments, the administering comprises three doses of the vaccine, at least two of the doses being spaced at least 1, 2, 3, 4, 5, 6, 7, 8, 9, 10, 11, 12, 13, 14, 15, 16, 17, 18, 19, 20, or 21 days apart and each dose comprising 8.5 µmoles or more of the nucleic acid of SEQ ID NO: 1. In some embodiments, the CCHFV is from Clade I, II, III, IV, V, VI, or VII. In some embodiments, the CC-IFV comprises, consists of, or consists essentially of IbAr 10200 or Afg09-2990.

In some embodiments, a vaccine is provided, the vaccine comprising a vector comprising a promoter and the nucleic acid of SEQ ID NO: 3, the nucleic acid of SEQ ID NO: 3 being operably linked to the promoter.

In some embodiments, a method is provided, the method comprising administering a vaccine comprising a vector comprising a promoter and the nucleic acid of SEQ ID NO: 3, the nucleic acid of SEQ ID NO: 3 being operably linked to the promoter.

In some embodiments, the vector comprises, consists of, consists essentially of, or is RNA or DNA. In some embodiments the nucleic acid of SEQ ID NOs: 1 and 3 comprise, consist of, consist essentially of, or is RNA or DNA.

In some embodiments the vector comprises, consists of, consists essentially of, or is SEQ ID NO: 1 or SEQ ID NO: 3.

In some embodiment the vaccine is co-administered with an effective amount of an adjuvant, wherein the adjuvant is an inorganic compound, an oil, a bacterial product, or a cytokine. In some embodiments the vaccine contains a pharmaceutically acceptable substance, wherein the substance is a carrier, additive, or excipient.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein. Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Methods

Ethics Statement

Research was conducted under a USAMRIID IACUC supported and approved protocol in compliance with the Animal Welfare Act, PHS Policy, and other Federal statutes and regulations relating to animals and experiments involving animals. The facility where this research was conducted is accredited by the AAALAC International and adheres to principles stated in the Guide for the Care and Use of Laboratory Animals, National Research Council, 2011[24]. Humane endpoints were used during these studies, and mice that were moribund, according to an endpoint score sheet, were humanely euthanized. Mice were euthanized by $CO_2$ exposure using compressed $CO_2$ gas followed by cervical dislocation. However, even with multiple observations per day, some animals died as a direct result of the infection.

Virus Production

CCHFV-IbAr 10200 virus was passaged nine times in suckling mouse brain and then propagated three times in Hep G2 cells. The virus was collected from clarified cell culture supernatants and stored at −80° C. CCHFV-Afg09-2990 virus was derived from a fatal human case in a U.S. soldier stationed in Afghanistan in 2009. CC-IFV-Afg09-2990 was passaged three times in Vero cells and then propagated twice in Huh-7 cells (Bernhard Nocht Institute)[25]. Harvested virus was collected from clarified cell culture supernatants and stored at −80° C. All CCHFV work was performed in BSL-4 containment.

CCHFV DNA Vaccine Construction

The M-segment ORF of strain CCHFV-IbAr 10200 was optimized by GeneArt for human codon usage and deletion of known motifs that are detrimental to mRNA stability or expression (SEQ ID NO: 1; FIG. 12). The optimized gene was de novo synthesized and cloned into pCAGGS. The codon-optimized M-segment ORF was subcloned into the mammalian expression vector pWRG7077 at the NotI sites to create the optimized CCHFV-$M_{10200}$ DNA vaccine[26] (SEQ ID NO: 2; FIG. 13). For the CCHFV-$M_{Afg09}$ DNA vaccine, The M-segment ORF of strain CCHFV-Afg09-2990 was optimized by ATUM Inc. (SEQ ID NO: 3; FIG. 14) and subcloned into pWRG7077 (SEQ ID NO: 4; FIG. 15). All nucleotide sequences were confirmed prior to vaccination.

DNA Vaccination and Viral Challenge in Mice

The C57BL/6 mice weighed 18.5+/−0.9 (st. dev.) g at 6 weeks of age; 19.0+/−1.0 g at 7 weeks of age; 19.6+/−1.2 g at 8 weeks of age; 20.3+/−13 g at 9 weeks of age; 20.7+/−1.4 g at 10 weeks of age; 21.3+/−1.5 g at 11 weeks of age; 21.9+/−1.6 g at 12 weeks of age; 22.6+/−1.9 g at 13 weeks of age; and 23.0+/−2.0 g at 14 weeks of age. Between 8-10 weeks of age, groups of 10 C57BL/6 mice (The Jackson Laboratory) were vaccinated three times at 3-week intervals with 50 μg (8.5 μmoles) of the pWRG7077 DNA vaccine plasmid expressing the codon-optimized M-segment from either CCHFV-IbAr 10200 (CCHFV-$M_{10200}$) or CCHFV-Afg09-2990 (CCHFV-$M_{Afg09}$) by IM-EP. Control groups of 10 C57BL/6 mice (The Jackson Laboratory) were vaccinated concurrently by IM-EP with pWRG7077 empty vector. For IM-EP delivery, mice were anesthetized and then vaccinated in the tibialis anterior muscle with 20 μL (50 μg total) of DNA solution using a ³⁄₁₀ cm3 U-100 insulin syringe inserted into the center of an Ichor Medical Systems TriGrid electrode array (Ichor Medical Systems) with 2.5 mm electrode spacing. Injection of DNA was followed immediately by electrical stimulation at an amplitude of 250 V/cm, and the total duration was 40 ms over a 400 ms interval. Sera were collected prior to vaccination on days 0, 21, and 42 by submandibular bleed. A cohort of mice was euthanized on day 49 for T cell analysis. The remainder of mice were observed until day 63, when sera were harvested for antibody analysis. Mice were subsequently challenged on day 72. For challenge, all mice were treated by the IP route with mAb-5A3 (Leinco Technologies Inc.) 24 h prior to (2.0 mg) and 24 h after (0.5 mg) CCHFV challenge. IS C57BL/6 mice were challenged with 100 PFU of CCHFV strain CCHFV-IbAr 10200 or 100 PFU of CCHFV-Afg09-2990 by the IP route. The mice were monitored daily for weight changes, clinical score, and survival. Twenty-six days following challenge, the surviving mice were euthanized by exsanguination under deep anesthesia.

CCHFV Cell Lysate

T150 flasks with HEK293T cells (ATCC) at 70-80% density were transfected with 15 μg of CCHFV-$M_{10200}$ or CCHFV-$M_{Afg09}$ using Fugene 6 (Promega) according to manufacturer's instructions. Cells were incubated for 48 hours at 37° C. in 5% $CO_2$ prior to being lifted by pipetting in media. Cell-laden media were then pelleted at 1,155×g for 5 minutes at 4° C. Supernatant was discarded and cells were washed two times sequentially with cold PBS (Gibco Life Technologies Corp). After final pelleting, the PBS was discarded and cells were lysed with 3 ml of lysis buffer per flask equivalent. Lysis buffer was as follows: 20 mM HEPES (Sigma-Aldrich), 110 mM Potassium Acetate (Sigma-Aldrich), and 2 mM, Magnesium Chloride (Sigma-Aldrich) supplemented with 1% Tween-20 (Sigma-Aldrich) and protease inhibitor tablets (Sigma-Aldrich). Cells were vortexed for 30 seconds and then lysed on a rocking platform overnight at 4° C. Debris was cleared at 16,100×g for 10 minutes at room temperature. Cleared lysate was then stored in single-use aliquots at −80° C. until use in ELISA.

CCHFV Cell Lysate ELISA

For cell lysate ELISA, High Bind ELISA plates (Corning) were coated overnight at 4° C. with a 1:4 dilution of CCHFV cell lysates diluted in PBS. The following day, plates were washed with PBS containing 0.05% Tween-20 (PBST) (Sigma-Aldrich) and then blocked with PBST containing 3% goat serum (Sigma-Aldrich) and 3% skim milk (BD Biosciences) for 1 hour at 37° C. Plates were washed with PBST again, prior to being loaded with two-fold serial dilutions of mouse sera in duplicate (dilution range 1:200 to 1:25,600). Sera were diluted in blocking buffer. Plates were incubated at ambient temperature for 1 hour prior to being washed with PBST, and then incubated with a 1:1000 dilution of horseradish peroxidase (HRP) conjugated goat anti-mouse (SeraCare Life Sciences) in PBST for 1 hour at ambient temperature. Plates were washed with PBST again and then developed with TMB substrate (SeraCare Life Sciences). Absorbance at the 450 nm wavelength was detected with a Tecan M1000 microplate reader (Tecan Group Ltd). Pooled naïve sera collected prior to vaccination were used as an internal control for each assay group. A plate cutoff value was determined based on the average absorbance of the naïve control starting dilution plus 3 standard deviations. Only sample dilutions whose average were above this cut-off were registered as positive signal. Additional analysis was carried out using GraphPad Prism 6 (GraphPad Software).

T-Cell ELISPOT

Mouse T cell ELISPOT reagents were obtained from Mabtech (Mabtech). Antigen specific IFN-$\gamma^+$ and IL-2$^+$ T cells were quantified per manufactures instructions. Positive control wells were stimulated with 10 ng/ml PMA (Sigma-Aldrich) and 500 ng/ml ionomycin (Sigma-Aldrich). Test splenocyte wells were stimulated with the appropriate peptides at a concentration of 2.5 μg/ml. Cells were incubated for 20 hours at 37° C. in 5% $CO_2$. Positive spots were visualized on a CTL Imager and counting was performed with Immunospot software (Cellular Technology Ltd.). Splenocytes from vaccinated mice were stimulated with pooled 15-mer peptides (9 pools of 17 peptides and 1 pool of 15 peptides) containing a 5-base overlap spanning the either the CCHFV-IbAr 10200 or CCHFV-Afg09-2990 M-segment open reading frames (Mimotopes).

Cloning

All GP38 constructs were produced through de novo synthesis (Genewiz). tPA-GP38 strain CCHFV-IbAr 10200 (NC_005300) was produced by the addition of the tPA secretion signal (MDAMKRGLCCVLLLCGAVFVSPS). Genes were cloned into the NotI and BglII sites of the pWRG7077 vector and verified by sequence analysis. For the histidine-tagged version of tPA-GP38 from strain CCHFV-IbAr 10200, six histidine residues were added to the C-terminal domain of the protein by de novo synthesis and cloned into the HindIII and XhoI site of pBFksr-HCacc-MCS, which contains a cytomegalovirus promotor (Biofactora).

A modified M-segment lacking the mucin and GP38 regions was produced by polymerase chain reaction (PCR). ΔMUCΔGP38 was produced using the forward primer 5'-ATCGCTGGGCTCCTCGCTGTGGCTGCCGTGGGTCTC-3' and reverse primer 3'-GAGACCCACGGCAGC-CACAGCGAGGAGCCCAGCGAT-5', which removed nucleotide regions 120 to 1545. The AMUCAGP38 construct retained the signal sequences 1 to 117. All PCR reactions were performed using the Phusion polymerase (Invitrogen). Following PCR, fragments were digested with NotI and BglII and ligated into the pWRG7077 vector. Sequence analysis was used to verify that the changes had been successfully incorporated into the gene.

GP38 Purification

Production of recombinant CCHFV-IbAr 10200 GP38his was accomplished by transient transfection of HEK293T cells (American Type Culture Collection) with the tPA-GP38his plasmid using FuGENE 6 (Promega) according to the manufacturer's instructions as previously described[17].

GP38 ELISA 500 ng per well of purified GP38, diluted in 0.1 M carbonate buffer (pH 9.6), was plated on a high-binding 96-well plate (Corning) and incubated overnight at 4° C. Plates were blocked for 2 hours in blocking buffer (PBST containing 5% milk) at 37° C. Plates were washed four times in PBST and incubated with mouse sera diluted in blocking buffer overnight at 4° C. (dilution range 1:200 to 1:25,600). Plates were washed four times in PBST and incubated with anti-mouse IgG conjugated to horseradish peroxidase diluted 1:1000 (Sigma-Aldrich) for 1 hour at 37° C. Plates were washed again four times in PBST, and 50 μl of ABTS microwell peroxidase 1-component (KPL) was added to each well. Reactions were stopped by adding 50 μl of ABTS stop solution (KPL). The optical density (OD) at 405 nm was read on a Tecan microplate reader (Tecan Group Ltd.).

MAGPIX Cytokine Assay

Murine cytokines/chemokines were assayed using a Luminex MAGPIX-based magnetic bead kit (EMD Millipore). Twenty-five cytokines (G-CSF, GM-CSF, IFN-γ, IL-1a, IL-10, IL-2, IL-4, IL-5, IL-6, IL-7, IL-9, IL-10, IL-12 (p40), IL-12 (p70), IL-13, IL-15, IL-17, IP-10, KC, MCP-1, MIP-la, MIP-10, MIP-2, RANTES, TNFα) were analyzed. Assay plates were prepared as per manufacturer's instructions. Briefly, 25 μL of prepared standards and controls were added to the appropriate wells of a 96-well round bottom plate. Next, 25 μL of MAGPIX assay buffer was added to background wells and all sample wells. Sera samples, prepared in duplicate, were diluted 1:5 in MAGPIX serum matrix diluent with 25 μL of this preparation added to the appropriate wells. The serum matrix diluent was also added to the background, standard, and controls, 25 μL per well. Pre-mixed magnetic cytokine/chemokine detection beads were vortexed and added to all wells, 25 μL per well. The plates were sealed and covered with foil to protect the contents from light and allowed to incubate on a digital plate shaker (IKA) overnight at 4° C. Following two washes with 200 μL per well of the MAGPIX sodium dodecyl sulfate (SDS) wash buffer, 25 μL of detection antibodies were added to all wells and incubated on a digital plate shaker for 1 hour at room temperature. A streptavidin-phycoerythrin solution was then added to all wells, 25 μL per well, and incubated on a digital plate shaker for 30 minutes at room temperature. Plates were washed twice with 200 μL per well of SDS buffer. The premixed beads were re-suspended in 150 μL of Bio-Plex MAGPIX Drive Fluid (Bio-Rad), and placed on a digital plate shaker for 5 minutes at room temperature. The plates were assayed on the MAGPIX instrument using Millipore xPONENT software (Luminex Corporation). The mean fluorescent intensity (MFI) for each sample was captured and analyzed using a 5-parameter logistic standard curve corrected for background. Sera dilutions were factored into the final data output.

Statistics

All data analysis was conducted with GraphPad Prism v8.3.1 for Windows. Data is presented as the mean of individual mice+/−the standard deviation (SD). Vaccine immunogenicity statistical analysis was performed using a Student's t test, a one-way ANOVA followed by a Tukey post-test, or a two-way ANOVA with Sidak's multiple comparison as indicated. Kaplan Meier survival curve analysis using a log rank test was performed to determine p value significance of vaccinated groups surviving lethal challenge compared to the control group.

Results

CCHFV-$M_{10200}$ Protects Mice from Homologous Challenge.

In earlier studies, we demonstrated partial protection against homologous CCHFV challenge in mice vaccinated with CCHFV-$M_{10200}$. To test the protective efficacy of our CCHFV-$M_{10200}$ vaccine, groups of 10 C57BL/6 mice were vaccinated three times, three weeks apart, with 50 μg of our CCHFV-$M_{10200}$ DNA vaccine (8.5 μmoles) or an empty vector control by IM-EP as described in the Methods. Four weeks following the final vaccination, the mice were treated with mAb-5A3 to block IFN-I signaling and challenged via the intraperitoneal (IP) route with 100 plaque forming units (PFU) of the homologous laboratory strain, CCHFV-IbAr 10200. The CCHFV-$M_{10200}$ vaccine provided 100% protection against CCHFV-IbAr 10200 challenge (FIG. 1A), with no signs of illness (lethargy, ruffling). Conversely, all empty vector controls developed visible signs of illness and succumbed to infection or reached euthanasia criteria by 4.5 days post-infection. The CCHFV-$M_{10200}$ vaccinated group had minimal transient weight loss in comparison to the empty vector control group (FIG. 1B).

Figure 2A:
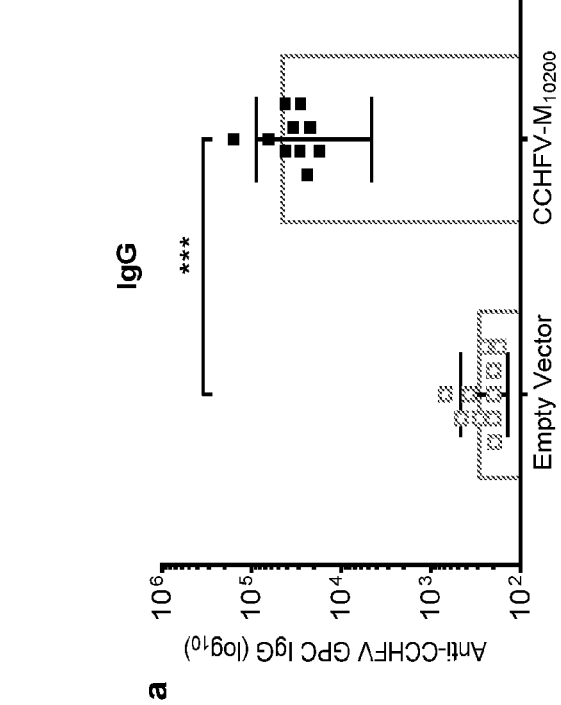
FIGS. 2A and 2B: CCHFV-$M_{10200}$ DNA vaccination elicits CCHFV-IbAr 10200 specific antibodies. Groups of 10 female C57BL/6 mice were vaccinated with 50 μg CCHFV-$M_{10200}$ (8.5 μmoles) or empty vector on days 0, 21, and 42 by IM-EP.
Figure 2B:
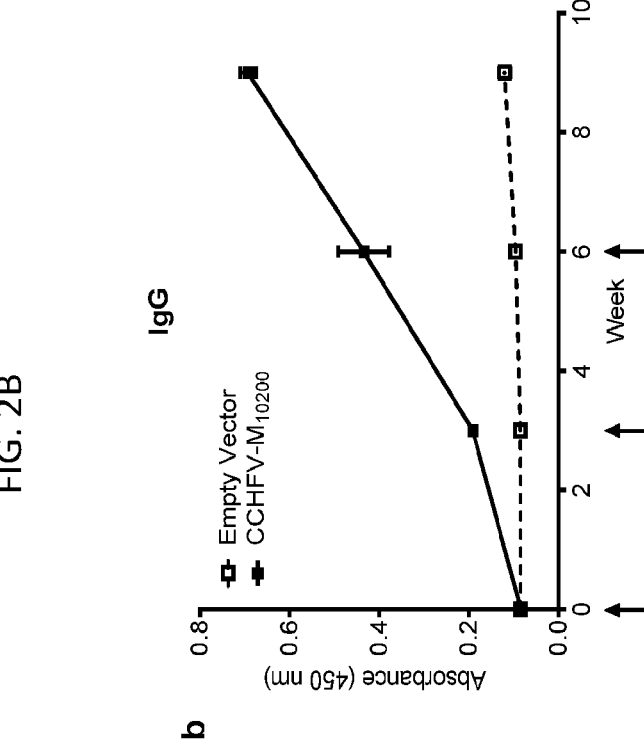

The CCHFV-$M_{10200}$ DNA vaccine elicits antigen-specific cellular and humoral immunity. As our CCHFV-$M_{10200}$ vaccine conferred complete protection against viral challenge, we investigated the possible immune correlates of protection. We initially quantified the antibody response elicited by our CCHFV-$M_{10200}$ DNA vaccine. For this analysis, we utilized lysates from CCHFV-IbAr 10200 CCHFV$_{VLP}$ transfected cells. The choice to use cell lysates instead of secreted CCHFV$_{VLP}$ was to capture the antibody responses to both the structural and non-structural proteins. IM-EP delivery of the CCHFV-$M_{10200}$ vaccine yielded high-level, CCHFV GPC-specific antibody titers (FIG. 2A) that were boosted by each subsequent vaccination (FIG. 2B). These data suggest that at a minimum, three vaccinations are required to reach the peak antibody response.

To examine the T-cell response elicited by the CCHFV-$M_{10200}$ DNA vaccine, we vaccinated a cohort of mice (n=9) three times as above, and one week following the final vaccination splenocytes were isolated for IFN-γ$^+$ and IL-2$^+$ T cell ELISPOT. Splenocytes were stimulated with ten individual peptide pools spanning the length of the CCHFV-IbAr 10200 M-segment open reading frame. The majority of IFN-γ$^+$ (FIGS. 3A and 3C) and IL-2$^+$ (FIGS. 3B and 3D) T-cell responses were mapped to the mucin-like domain (MLD) and GP38 non-structural proteins, as well as to $NS_M$ and the N-terminus of $G_C$. Peptide pools spanning $G_N$ did not stimulate an antigen-specific T cell response. We also quantified cytokine signaling in CCHFV-$M_{10200}$ vaccinated mice from sera harvested at the time of euthanasia. CCHFV-$M_{10200}$ vaccinated mice had significant increases in the $T_h1$ cytokines TNF-$\alpha$ and IL-12, and the Th2 cytokine IL-6 after three vaccinations (FIGS. 10A, 10B, 10C, and 10D). These results further demonstrate the ability of DNA vaccines to elicit balanced adaptive immune responses.

Vaccination with the CCHFV-$M_{10200}$ DNA Vaccine Generates Cross-Clade Immunity, and is Partially Protective Against Heterologous Challenge.

Since our CCHFV-IbAr 10200 vaccine was completely protective against homologous challenge, we tested the cross-protective efficacy of the CCHFV-$M_{10200}$ DNA vaccine against a clinically relevant strain, CCHFV-Afg09-2990, from a divergent clade of CCHFV strains. Groups of 20 C57BL/6 mice were vaccinated with 50 µg of our CCHFV-$M_{10200}$ DNA vaccine (8.5 µmoles), three times, three weeks apart, or an empty vector control by IM-EP as described in the Methods. One week after the final vaccination, 10 mice from each group were euthanized for T cell ELISPOT analysis. Splenocytes were stimulated with peptide pools spanning the CCHFV-Afg09-2990 M-segment open-reading frame, and the IFN-$\gamma^+$ (FIGS. 4A and 4C) and IL-2$^+$ (FIGS. 4B and 4D) T cell responses were quantified. Unexpectedly, the pools spanning the MLD of CCHFV-Afg09-2990 did not elicit a T-cell response in CCHFV-$M_{10200}$ vaccinated mice, and one pool (Pool #3) spanning GP38 elicited only a minimal response. CCHFV-$M_{10200}$ vaccination unexpectedly elicited potent T cell responses directed against the CCHFV-Afg09-2990 pools spanning the $NS_M$ and N-terminal domain of $G_C$, similar to the response seen in splenocytes stimulated with the homologous CCHFV-IbAr 10200 peptides.

Figure 5A:
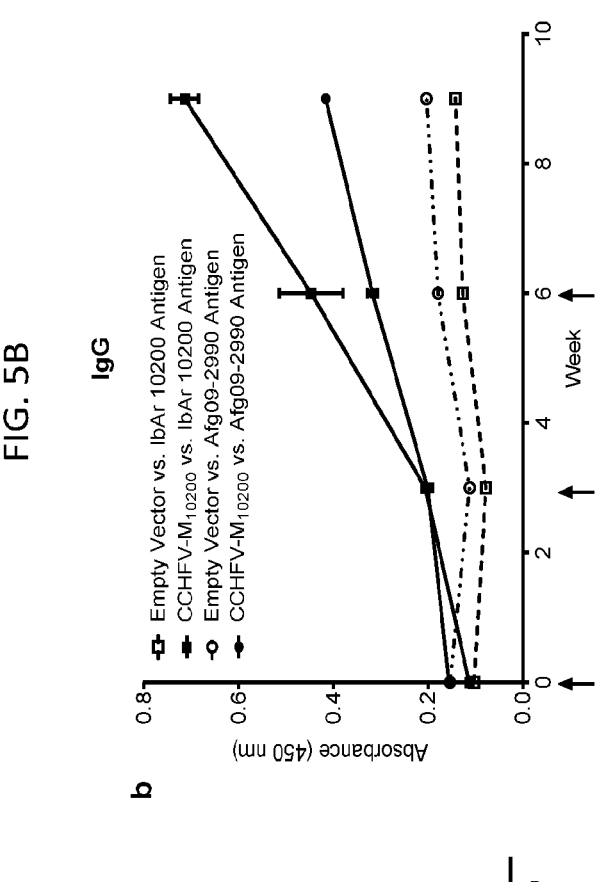
FIGS. 5A and 5B: CCHFV-$M_{10200}$ DNA vaccination elicits antibodies that are partially cross-reactive to CCHFV-Afg09-2990. Groups of 10 female C57BL/6 mice were vaccinated with 50 μg CCHFV-$M_{10200}$ (8.5 μmoles) or empty vector on days 0, 21, and 42 by IM-EP.
Figure 5B:
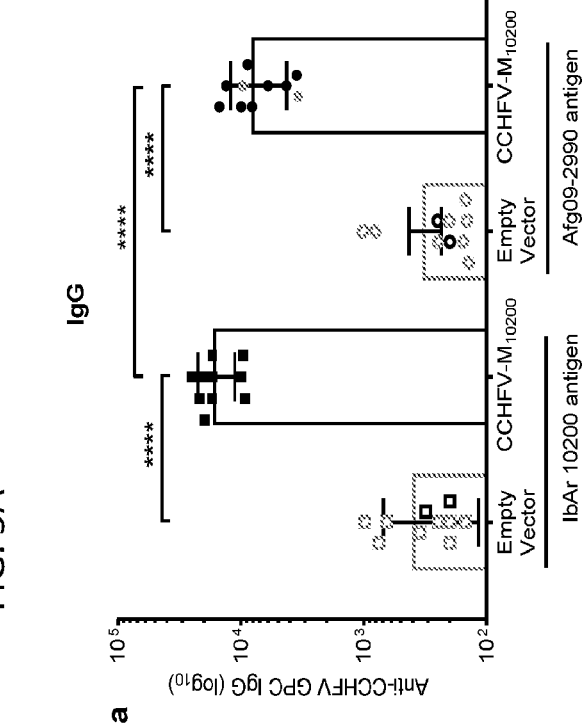

We then followed the remaining mice (n=10) for an additional two weeks to assess the development of anti-CCHFV antibodies. For this analysis, we tested sera from CCHFV-$M_{10200}$ vaccinated mice against not only CCHFV-IbAr 10200 antigen, but also CCHFV-Afg09-2990 antigen. All CCHFV-$M_{10200}$ vaccinated mice generated antibodies. CCHFV-$M_{10200}$ vaccination elicited significant anti-CCHFV-IbAr 10200 antibody titers. We unexpectedly observed significant antibody titers when the same sera were tested against the CCHFV-Afg09-2990 antigen (FIG. 5A). Anti-CCHFV-Afg09-2990 antibody levels were further boosted after each vaccination. They remained significantly below the level measured against CCHFV-IbAr 10200 antigen, suggesting at least a partial divergence in humoral epitopes (FIG. 5B).

Figure 6B:
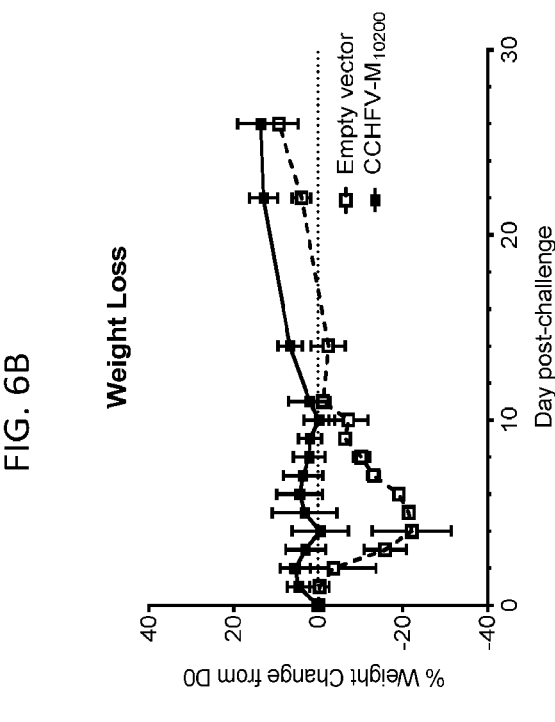
FIGS. 6A and 6B: CCHFV-$M_{10200}$ DNA vaccination provides significant protection against heterologous challenge. Groups of 10 female C57BL/6 mice were vaccinated with 50 μg CCHFV-$M_{10200}$ (8.5 μmoles) or empty vector on days 0, 21, and 42 by IM-EP. Group survival (FIG. 6A) and weight change (FIG. 6B) following CCHFV challenge with 100 PFU by the IP route with the heterologous CCHFV- Afg09-2990 strain. Vaccinated C57BL/6 mice were transiently immunosuppressed prior to challenge. **$p<0.01$. The percent survival p value was determined by a log rank test.
Figure 6A:
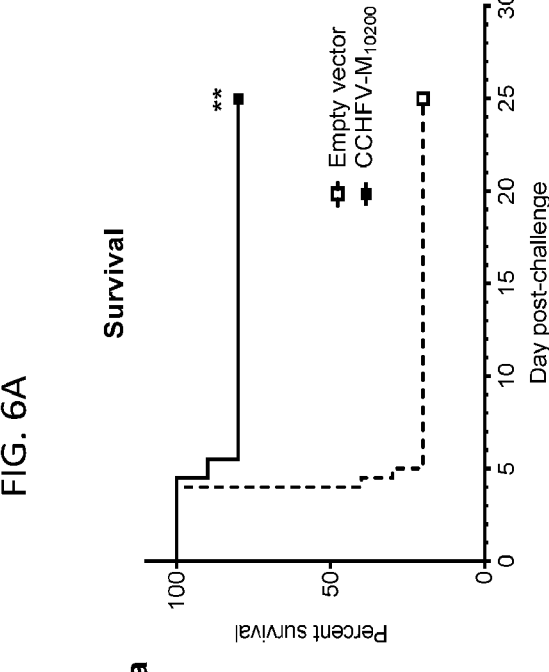

Four weeks after the final vaccination, all remaining mice were treated by IP injection with mAb-5A3 and challenged by IP injection of 100 PFU CCHFV-Afg09-2990. Two mice in the empty vector group survived challenge with strain CCHFV-Afg09-2990 (FIG. 6A); however, these mice had significant weight loss and a ruffled appearance (FIG. 6B). The CCHFV-$M_{10200}$ DNA vaccine unexpectedly provided 80% protection against CCHFV strain CCHFV-Afg09-2990 (FIG. 6A), which was a significant survival rate when compared to that of the empty vector treated mice. Moreover, the two vaccinated mice that succumbed to CCHFV challenge had a delay in weight loss compared to the vector only control mice and did not display other signs of illness such as ruffled fur (FIG. 6B). There was no correlation between antibody titer and protection from CCHFV challenge. These results are unexpected as this is the first report of cross-clade and heterologous protection using a CCHFV DNA vaccine. As noted above, the other reports of cross-clade or heterologous protection used a virus-like replicon particle (VRP) vaccine expressing the GPC of the Oman-1998 strain tested against CCHFV-IbAr 10200 and a replication-competent recombinant vesicular stomatitis virus (rVSV) against the Turkey 200406546 strain. The protection against CCHFV-Afg09-2990 observed here is also more clinically relevant than protection against IbAr 10200.

A DNA Vaccine Expressing the CCHFV-Afg09-2990 M-Segment Completely Protects Against CCHFV-Afg09-2990 Challenge.

Figures 7A, 7B, 7C, 7D:
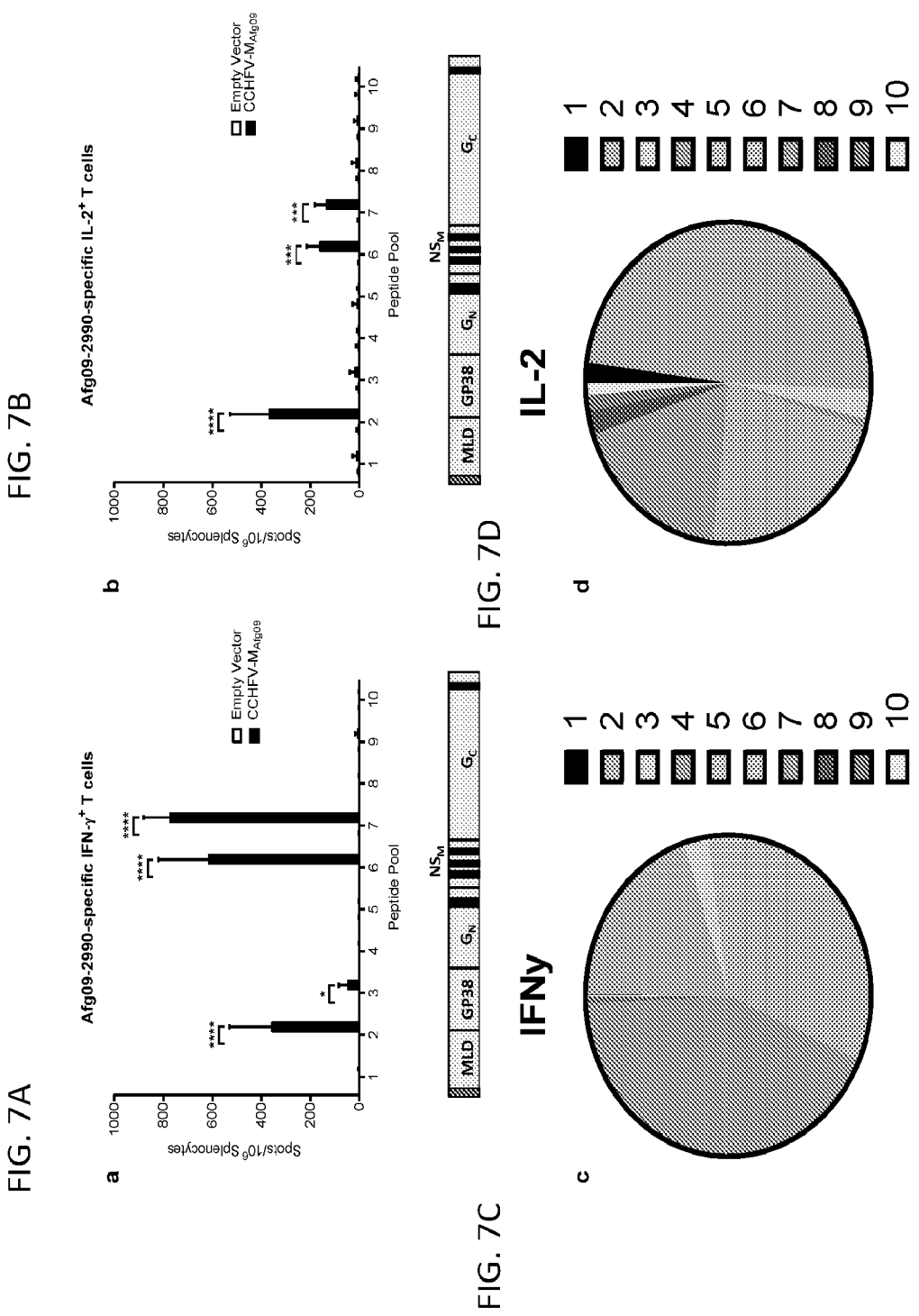
FIGS. 7A, 7B, 7C, and 7D: Anti-GP38 cellular immune responses are rescued following homologous CCHFV-$M_{Afg09}$ vaccination. Groups of 10 female C57BL/6 mice were vaccinated with 50 μg CCHFV-$M_{Afg09}$ or empty vector on days 0, 21, and 42 by IM-EP, and then euthanized on day 49 for splenocyte T cell analysis. Splenocytes from individual mice were re-stimulated with pooled peptides derived from the CCHFV-Afg09-2990 M-segment. Anti-CCHFV-M specific IFN-$\gamma^+$ (FIG. 7A) and IL-$2^+$ (FIG. 7B) T cells were quantified by ELISPOT. The corresponding region of the peptide pools to the M-segment are shown below each graph. Percentage of IFN-$\gamma^+$ (FIG. 7C) and IL-$2^+$ (FIG. 7D) T cells responding to each peptide pool. Data are the group mean averages+/−SD. *$p<0.05$; *$p<0.001$; *$p<0.0001$. p values were determined by two-way ANOVA with Sidak's multiple comparison test with a 95% confidence interval.

In an effort to improve upon the partial protection measured in CCHFV-$M_{10200}$ vaccinated mice challenged with CCHFV-Afg09-2990, we generated a DNA vaccine expressing the M-segment from CCHFV-Afg09-2990 (CCHFV-$M_{Afg09}$). Groups of 20 C57BL/6 mice were vaccinated with 50 µg of CCHFV-$M_{Afg09}$ DNA vaccine (8.5 µmoles) or empty vector control by IM-EP as described in the Methods. As above, 10 mice from each group were euthanized for T cell ELISPOT analysis one week post final vaccination. Splenocytes were stimulated with peptide pools spanning the CCHFV-Afg09-2990 M-segment open-reading frame, and the IFN-$\gamma^+$ (FIGS. 7A and 7C) and IL-2$^+$ (FIGS. 7B and 7D) T cell responses were quantified. Whereas CCHFV-$M_{10200}$ vaccinated mice only generated a T cell response to the CCHFV-Afg09-2990 $G_C$ segment, mice vaccinated with CCHFV-$M_{Afg09}$ developed significant levels of MLD, GP38, and $G_C$-specific T cells. Unexpectedly, CCHFV-$M_{Afg09}$ vaccination did not elicit a T cell response against CCHFV-Afg09-2990 MLD peptide Pool 1 as was measured in CCHFV-$M_{10200}$ vaccinated mice. These data suggest that elicitation of cellular immune responses against the GP38 domain may require homologous vaccination. Accordingly, the effects of the CCHFV-$M_{Afg09}$ vaccine are further unexpected over those with the CCHFV-$M_{10200}$ vaccine.

We continued to follow the remaining mice (n=10) for an additional two weeks to assess the development of anti-CCHFV-Afg09-2990 GPC antibodies. All CCHFV-$M_{Afg09}$ vaccinated mice seroconverted while empty vector controls failed to develop CCHFV-Afg09-2990 GPC-specific antibodies (FIGS. 8A and 8B). Four weeks after the final vaccination, all remaining mice were treated by IP injection of mAb-5A3 and challenged by 100 PFU of CCHFV-Afg09-2990. One mouse in the empty vector group survived challenge (FIG. 8C); however, this mouse exhibited approximately 24% weight loss and a ruffled appearance (FIG. 8D). In contrast, CCHFV-$M_{Afg09}$ completely protected all mice from challenge (FIG. 8C) with only transient weight loss (FIG. 8D).

GP38 DNA Vaccination Partially Protects Against CCHFV Challenge.

Figure 11:
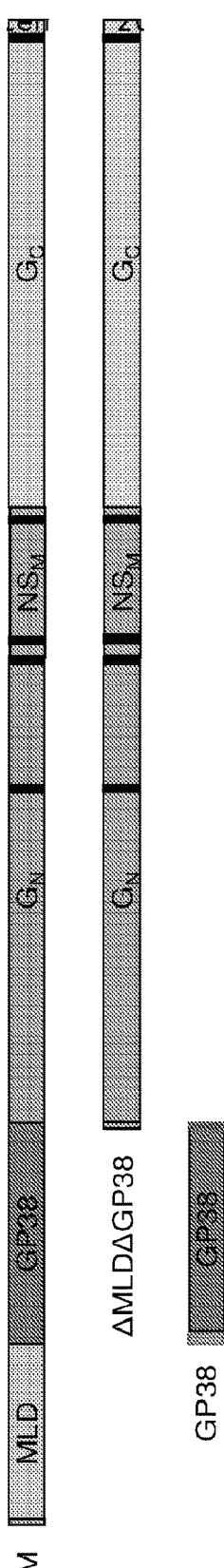
FIG. 11: Schematic representations of truncated CCHFV DNA vaccines.

As we found the most significant changes in immune profile between the CCHFV-$M_{10200}$ and CCHFV-$M_{Afg09}$ vaccine in the MLD and the GP38 regions, without wishing to be bound to a particular theory, we hypothesized that a DNA vaccine expressing the GP38 region of CCHFV-IbAr 10200 would confer protection against homologous challenge. We therefore tested plasmids expressing either CCHFV-IbAr 10200 GP38, or a truncated CCHFV-IbAr 10200 M-segment with deleted MLD and GP38 regions ($\Delta$MLD$\Delta$GP38) as DNA vaccines (FIG. 11). Groups of mice (n=10) were vaccinated three times with 50 µg of CCHFV-$M_{10200}$ (8.5 µmoles), GP38, or $\Delta$MLD$\Delta$GP38 DNA vaccines by IM-EP. A control group of mice received 50 µg of empty vector. Three weeks after the final vaccination, we quantified both total anti-CCHFV-IbAr 10200 GPC (FIG. 9A) and anti-CCHFV-IbAr 10200 GP38-specific (FIG. 9B) IgG. Vaccination with full-length CCHFV-$M_{10200}$ elicited antibodies to both GPC and GP38 proteins. ΔMLDΔGP38 vaccinated mice had anti-CCHFV GPC antibodies, but did not have significant levels of antibodies directed against GP38 as expected. GP38 vaccinated mice exhibited similar levels of anti-GP38-specific antibodies to the CCHFV-$M_{10200}$ group.

Figures 9A, 9B, 9C, 9D, 9E:
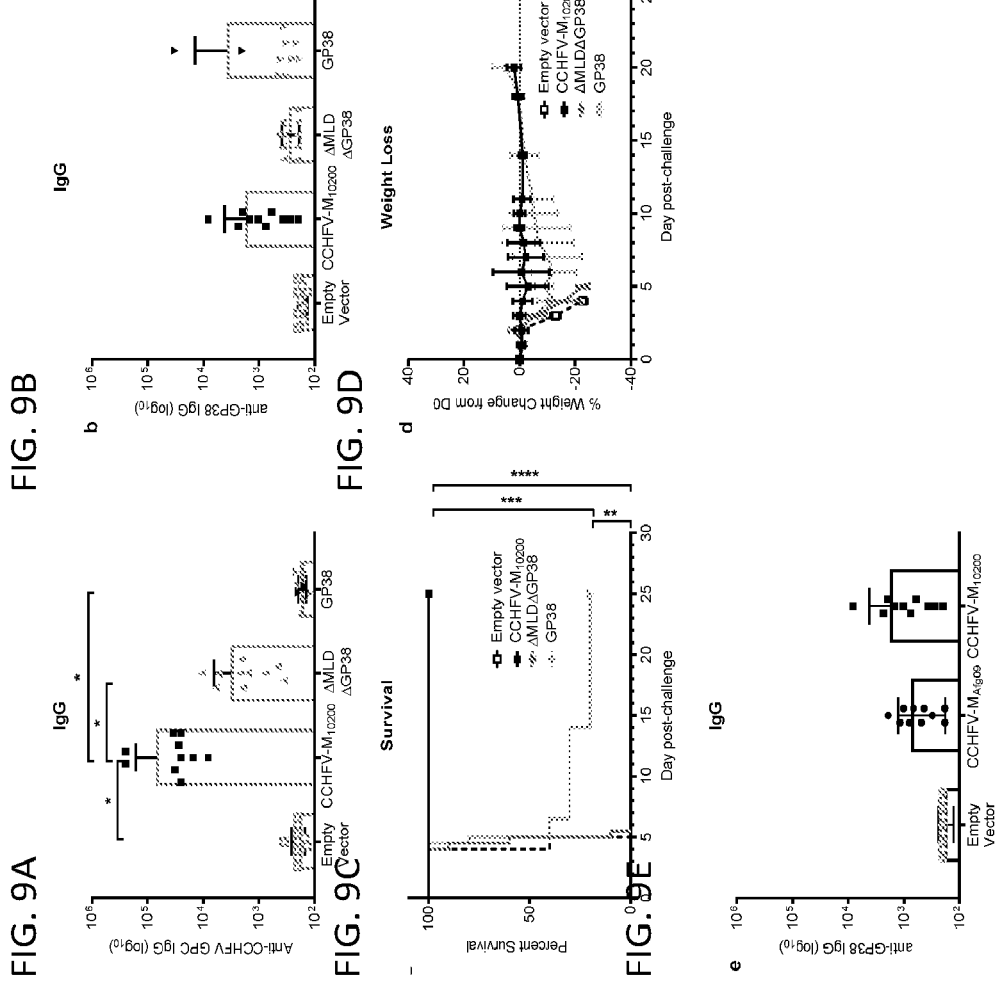
FIGS. 9A, 9B, 9C, 9D, and 9E: GP38 vaccination is partially protective against homologous challenge. Groups of 10 female C57BL/6 mice were vaccinated with 50 μg CCHFV-$M_{10200}$ (8.5 μmoles), ΔMLDΔGP38, or GP38 on days 0, 21, and 42 by IM-EP.
Figures 10A, 10B, 10C, 10D:
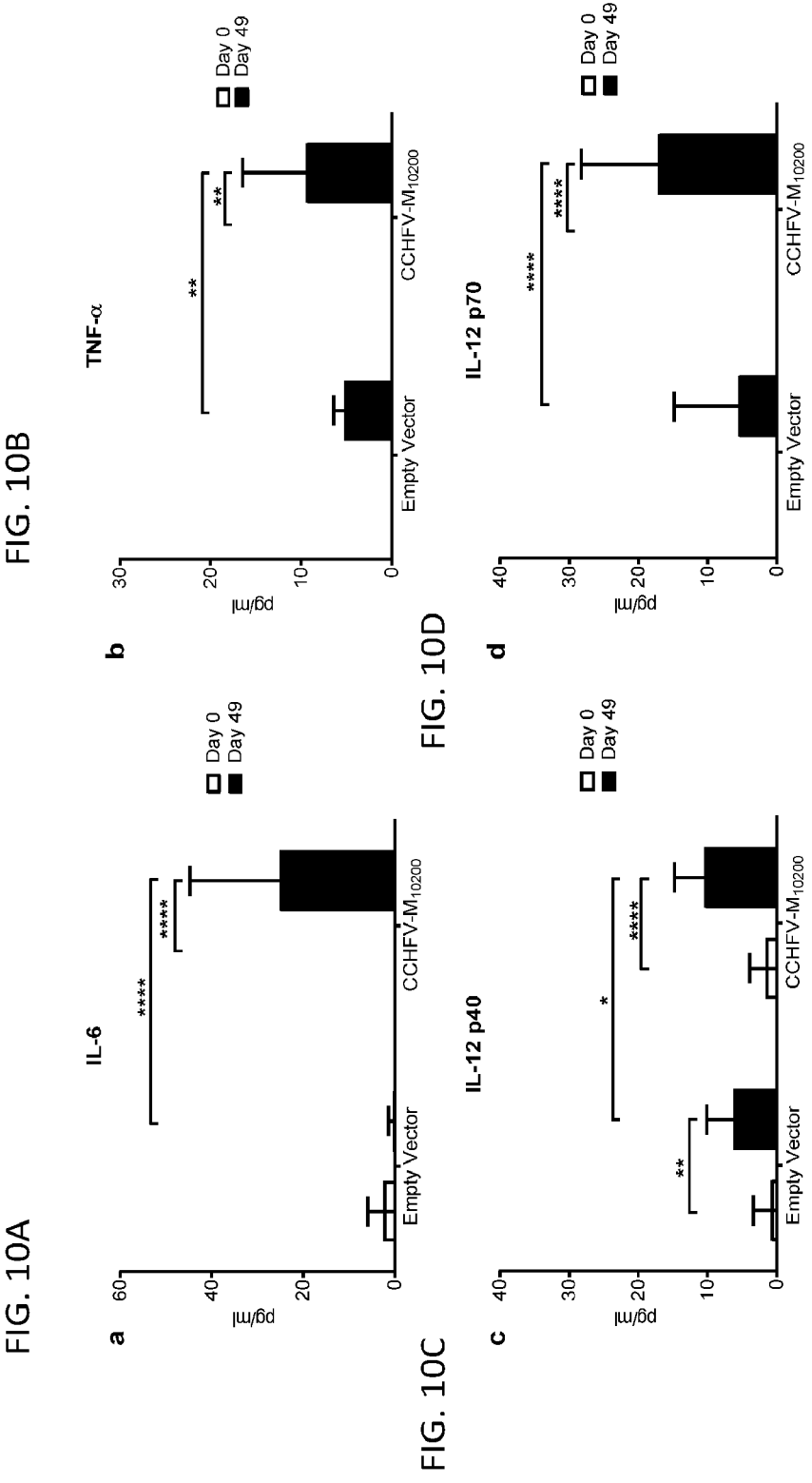
FIGS. 10A, 10B, 10C, and 10D: CCHFV-$M_{10200}$ vaccination stimulates Th1 and Th2 cytokine signaling. 10 female C57BL/6 mice were vaccinated with 50 μg (8.5 μmoles) CCHFV-$M_{10200}$ on days 0, 21, and 42 by IM-EP, and then euthanized on day 49. Sera were collected at the time of euthanasia and IL-6 (FIG. 10A), TNF-α (FIG. 10B), IL-12 p40 (FIG. 10C), and IL-12 p70 (FIG. 10D) cytokine levels were quantified by Luminex assay. Shown are significant differences in cytokines after vaccination. Data are the group mean averages+/−SD. *p<0.05; p<0.01; **p<0.0001. p values were determined by one-way ANOVA with 'Tukey's post hoc test with a 95% confidence interval.

Four weeks after the final vaccination, all mice were treated by IP injection of mAb-5A3 and challenged by IP injection of 100 PFU of CCHFV-IbAr 10200. All mice in the empty vector group became moribund and succumbed to infection or were euthanized (FIG. 9C). All CCHFV-$M_{10200}$ vaccinated mice survived challenge and maintained weight throughout the study (FIG. 9D). Two GP38 vaccinated mice survived viral challenge without developing overt signs of disease, and a third had a delayed time to death. The two surviving mice had the highest anti-GP38 antibody titers. Surprisingly, all ΔMLDΔGP38 vaccinated mice succumbed to infection at an equivalent rate to the empty vector group. These results suggest that high levels of anti-GP38 antibodies can provide protection from CCHFV challenge, while $G_N/G_C$ epitopes alone do not elicit sufficient immunity for protection.

Finally, we compared the anti-CCHFV-IbAr 10200 GP38 antibody response from CCHFV-$M_{10200}$ and CCHFV-$M_{Afg09}$ vaccinated mice (FIG. 9E). Anti-GP38 titers in CCHFV-$M_{Afg09}$ vaccinated mice trended approximately two fold lower than did titers measured in CCHFV-$M_{10200}$ vaccinated mice, suggesting that the humoral response directed against GP38 is at least partially strain specific.

Discussion

DNA vaccines elicit high levels of humoral and cellular immunity[18]. This is especially important in instances when the immune correlate of protection remains unknown, as is the case with CCHF. It was previously established that DNA vaccines can completely protect mice from homologous CCHFV challenge[10]. However, that vaccine consisted of three separate plasmids ($G_N$, $G_C$, N) delivered as a mixed formulation. Here we report single plasmid vaccines expressing full-length M-segments of two diverse CCHFV strains. This approach provides three key benefits: 1) it ensures that all transfected cells receive the necessary components to express structurally relevant CCHFV glycoprotein; 2) it generates immunity to multiple M-segment epitopes; and 3) it streamlines vaccine production and scale up.

Here we tested a 50 µg dose of CCHF-$M_{10200}$ (8.5 µmole), and also developed a vaccine based on the clinically relevant CCHFV-Afg09-2990 strain (CCHFV-$M_{Afg09}$). Both the CCHFV-$M_{10200}$ and CCHFV-$M_{Afg09}$ vaccines were highly immunogenic, eliciting significant anti-CCHFV GPC humoral and cellular immune responses, and completely protected mice against their respective homologous challenges. These results provide evidence that the CCHFV M-segment alone is sufficient for balanced, protective immunity. Of note, several vaccines have included N in their formulation[10, 13], but the absence of N in our vaccines did not negatively impact protective efficacy, as all mice survived homologous challenge.

The protective targets for a CCHF vaccine remain unclear, but our results may provide some insight into the role defined M-segment antigenic regions play. It was reported that neutralizing and non-neutralizing antibodies directed against the unprocessed $G_N$ complex or the $G_C$ region of the glycoprotein can protect neonatal mice from CCHFV challenge, suggesting their potential as antibody targets[19]. We therefore predicted that our ΔMLDΔGP38 vaccine would confer some level of protection from challenge. A previous attempt to generate protective immunity with either $G_N$ or $G_C$ recombinant protein was unsuccessful[7], but we expected that plasmid vaccination would prove beneficial as expressing both proteins results in stable cell surface glycoprotein expression. However, there was no significant difference in time-to-death between the ΔMLDΔGP38 and empty vector groups. Our findings reflect the lack of in vivo protection in adult mice with antibodies targeting $G_C$[10, 17]. Why vaccination with $G_N/G_C$ alone does not confer protection remains unknown, especially as we measured potent anti-$G_C$ T cell responses in both CCHFV-$M_{10200}$ and CCHFV-$M_{Afg09}$ vaccinated mice and epitope mapping from clinical samples showed strong $G_N$ and $G_C$ reactivity[20]. These results hint that undefined epitopes within the M-segment may be critical for survival of vaccinated animals.

So what M-segment regions contribute to vaccine efficacy? The answer may partially lie in GP38. Pre-challenge treatment with mAb-13G8, a non-neutralizing monoclonal antibody directed against CCHFV-IbAr 10200 GP38, protected against homologous CCHFV challenge in mice. Here, we demonstrate partial, but significant, protection with a GP38-only vaccine. Mapping studies of B cell epitopes have identified the MLD and GP38 as key epitopic regions[10, 20]. We hypothesize that GP38 has a broad impact on protective efficacy in a strain specific manner. This hypothesis is supported by the partial protection measured in CCHFV-Afg09-2990 challenged mice vaccinated with CCHFV-$M_{10200}$. Interestingly, mice vaccinated with CCHFV-$M_{10200}$ had similar levels of anti-$G_N/G_C$ T cell responses following stimulation with either CCHFV-IbAr 10200 or CCHFV-Afg09-2990 peptides, but did not generate significant cellular immunity to the MLD or GP38 regions of CCHFV-Afg09-2990. The response to GP38 was rescued upon CCHFV-$M_{Afg09}$ vaccination, which protected 100% of the animals against CCHFV-Afg09-2990 challenge. Likewise, anti-CCHFV-IbAr 10200 GP38 titers trended lower in CCHFV-$M_{Afg09}$ vaccinated mice, and protection against heterologous viral strains can be limited following mAb-13G8 treatment. These results demonstrate that heterologous protection may be influenced by the route of treatment, timing, and regions of sequence divergence[17, 21]. Most notably, our GP38 DNA vaccine yielded 20% protection, a result that coincided with the two mice with the highest anti-GP38 antibody levels. The high genetic diversity of GP38 between different CCHFV strains may explain the decrease in protection. Based on our results herein and without wishing to be bound by a particular theory, it appears that subtle differences in the GP38 amino acid sequences can significantly affect both arms of the adaptive immune response. Small changes in amino acid sequence or secondary structures can limit antibody affinity, thereby reducing the effectiveness of neutralizing and non-neutralizing antibodies. Similarly, changes in the amino acid sequence can alter major histocompatibility complex (MHC) I or MHC II antigen presentation, impairing the stimulation of CD4$^+$ and/or CD8$^+$ effector lymphocytes. GP38 has at least three non-overlapping epitopes, and multiple regions may influence vaccine efficacy[17]. These results suggest that anti-GP38 immunity is critical for a positive challenge outcome. We recommend further studies to examine how GP38 genetic diversity impacts CCHFV infection.

In summary, here we show that a DNA vaccine expressing only the M-segment of CCHFV can provide complete protection from homologous challenge and can unexpectedly provide partial protection from heterologous challenge, depending upon the amount of vaccine provided. Our results demonstrate that the diminished protection is at least partially attributable to the genetic diversity of the GP38 region.

REFERENCES

The disclosures of each and every patent, patent application, and publication cited herein are hereby incorporated herein by reference in their entirety. While this invention has been disclosed with reference to specific embodiments, it is apparent that other embodiments and variations of this invention may be devised by others ordinarily skilled in the art without departing from the true spirit and scope of the invention. The appended claims are intended to be construed to include all such embodiments and equivalent variations.

1 Bente, D. A. et al. Crimean-Congo hemorrhagic fever: history, epidemiology, pathogenesis, clinical syndrome and genetic diversity. *Antiviral Res* 100, 159-189, doi:10.1016/j.antiviral.2013.07.006 (2013).

2 Schmaljohn, C. S. & Nichol, S. T. in *Fields Virology* Vol. 5th edn (ed Knipe D M and Howley P M) 1741-1789 (Lippincott Williams & Wilkins, 2007).

3 Blueprint for R&D preparedness and response to public health emergencies due to highly infectious pathogens. (World Health Organization, Geneva, Switzerland, 2015).

4 2018 Annual review of diseases prioritized under the Research and Development Blueprint. (World Health Organization, Geneva, Switzerland, 2018).

5 Shepherd, A. J., Swanepoel, R. & Leman, P. A. Antibody response in Crimean-Congo hemorrhagic fever. *Rev Infect Dis* 11 Suppl 4, S801-806, doi:10.1093/clinids/11.supplement_4.s801 (1989).

6 Swanepoel, R. et al. The clinical pathology of Crimean-Congo hemorrhagic fever. *Rev Infect Dis* 11 Suppl 4, S794-800, doi:10.1093/clinids/11.supplement_4.s794 (1989).

7 Kortekaas, J. et al. Crimean-Congo Hemorrhagic Fever Virus Subunit Vaccines Induce High Levels of Neutralizing Antibodies But No Protection in STAT1 Knockout Mice. *Vector Borne Zoonotic Dis* 15, 759-764, doi:10.1089/vbz.2015.1855 (2015).

8 Garrison, A. R. et al. A DNA vaccine for Crimean-Congo hemorrhagic fever protects against disease and death in two lethal mouse models. *PLoS Negl Trop Dis* 11, e0005908, doi:10.1371/journal.pntd.0005908 (2017).

9 Buttigieg, K. R. et al. A novel vaccine against Crimean-Congo Haemorrhagic Fever protects 100% of animals against lethal challenge in a mouse model. *PLoS one* 9, e91516, doi:10.1371/journal.pone.0091516 (2014).

Hinkula, J. et al. Immunization with DNA Plasmids Coding for Crimean-Congo Hemorrhagic Fever Virus Capsid and Envelope Proteins and/or Virus-Like Particles Induces Protection and Survival in Challenged Mice. *J Virol* 91, doi:10.1128/JVI.02076-16 (2017).

11 Dowall, S. D. et al. Protective effects of a Modified Vaccinia Ankara-based vaccine candidate against Crimean-Congo Haemorrhagic Fever virus require both cellular and humoral responses. *PLoS one* 11, e0156637, doi:10.1371/journal.pone.0156637 (2016).

12 Rodriguez, S. E. et al. Vesicular Stomatitis Virus-Based Vaccine Protects Mice against Crimean-Congo Hemorrhagic Fever. *Sci Rep* 9, 7755, doi:10.1038/s41598-019-44210-6 (2019).

13 Zivcec, M., Safronetz, D., Scott, D. P., Robertson, S. & Feldmann, H. Nucleocapsid protein-based vaccine provides protection in mice against lethal Crimean-Congo hemorrhagic fever virus challenge. *PLoS Negl Trop Dis* 12, e0006628, doi:10.1371/journal.pntd.0006628 (2018).

14 Aligholipour Farzani, T. et al. Immunological Analysis of a CCHFV mRNA Vaccine Candidate in Mouse Models. *Vaccines (Basel)* 7, doi:10.3390/vaccines7030115 (2019).

15 Canakoglu, N. et al. Immunization of knock-out alpha/beta interferon receptor mice against high lethal dose of Crimean-Congo hemorrhagic fever virus with a cell culture based vaccine. *PLoS neglected tropical diseases* 9, e0003579, doi:10.1371/journal.pntd.0003579 (2015).

16 Scholte, F. E. M. et al. Single-dose replicon particle vaccine provides complete protection against Crimean-Congo hemorrhagic fever virus in mice. *Emerg Microbes Infect* 8, 575-578, doi:10.1080/22221751.2019.1601030 (2019).

17 Golden, J. W. et al. GP38-targeting monoclonal antibodies protect adult mice against lethal Crimean-Congo hemorrhagic fever virus infection. *Sci Adv* 5, eaaw9535, doi:10.1126/sciadv.aaw9535 (2019).

18 Whalen, R. G. DNA vaccines for emerging infectious diseases: what if? *Emerg Infect Dis* 2, 168-175, doi:10.3201/eid0203.960302 (1996).

19 Bertolotti-Ciarlet, A. et al. Cellular localization and antigenic characterization of crimean-congo hemorrhagic fever virus glycoproteins. *J Virol* 79, 6152-6161, doi:10.1128/JVI.79.10.6152-6161.2005 (2005).

20 Fritzen, A. et al. Epitope-mapping of the glycoprotein from Crimean-Congo hemorrhagic fever virus using a microarray approach. *PLoS Negl Trop Dis* 12, e0006598, doi:10.1371/journal.pntd.0006598 (2018).

21 Mishra, A. K. et al. Structure and Characterization of Crimean-Congo Hemorrhagic Fever Virus GP38. *J Virol* 94, doi:10.1128/JVI.02005-19 (2020).

22 Burt, F. J. et al. Immunohistochemical and in situ localization of Crimean-Congo hemorrhagic fever (CCHF) virus in human tissues and implications for CCHF pathogenesis. *Arch Pathol Lab Med* 121, 839-846 (1997).

23 Lindquist, M. E. et al. Exploring Crimean-Congo Hemorrhagic Fever Virus-Induced Hepatic Injury Using Antibody-Mediated Type I Interferon Blockade in Mice. *J Virol* 92, doi:10.1128/JVI.01083-18 (2018).

24 Council, N. R. *Guide for the Care and Use of Laboratory Animals.* 8th edn, (National Academies Press, 2011).

25 Conger, N. G. et al. Health care response to CCHF in US soldier and nosocomial transmission to health care providers, Germany, 2009. *Emerg Infect Dis* 21, 23-31, doi:10.3201/eid2101.141413 (2015).

26 Spik, K. et al. Immunogenicity of combination DNA vaccines for Rift Valley fever virus, tick-borne encephalitis virus, Hantaan virus, and Crimean Congo hemorrhagic fever virus. *Vaccine* 24, 4657-4666, doi:10.1016/j.vaccine.2005.08.034 (2006).

We claim:

1. A vaccine comprising a vector comprising a promoter and the nucleic acid of SEQ ID NO: 3, the nucleic acid of SEQ ID NO: 3 being operably linked to the promoter.

2. The vaccine of claim 1, wherein the vector comprises the nucleic acid of SEQ ID NO: 4.

3. The vaccine of claim 1, wherein the vaccine further comprises an effective amount of an adjuvant.

4. The vaccine of claim 1, wherein the vaccine further comprises a pharmaceutically acceptable substance.

5. A method comprising administering a vaccine comprising a vector comprising a promoter and the nucleic acid of SEQ ID NO: 3, the nucleic acid of SEQ ID NO: 3 being operably linked to the promoter.

6. The method of claim 5, wherein the vector comprises the nucleic acid of SEQ ID NO: 4.

7. A method of increasing the likelihood of survival or decreasing the likelihood or severity of at least one symptom from a Congo-Crimean Hemorrhagic Fever Virus (CCHFV) in a subject in need thereof, the method comprising administering to the subject a vaccine comprising a vector comprising a promoter and 8.5 μmoles or more of the nucleic acid of SEQ ID NO: 1, wherein the nucleic acid of SEQ ID NO: 1 is operably linked to the promoter and wherein the administering provides at least a 60%, 70%, 80%, 90%, 95%, 96%, 97%, 98%, 99%, 99.8%, 99.9%, or 100% likelihood of survival in the subject five days after exposure to the CCHFV or the administering reduces the likelihood of a greater than 10% weight loss in the subject after exposure to the CCHFV.

8. The method of claim 7, wherein the administering comprises three doses of the vaccine, at least two of the doses being spaced at least 1, 2, 3, 4, 5, 6, 7, 8, 9, 10, 11, 12, 13, 14, 15, 16, 17, 18, 19, 20, or 21 days apart and each dose comprising 8.5 μmoles or more of the nucleic acid of SEQ ID NO: 1.

9. The method of claim 7, wherein the CCHFV is from Clade I, II, III, IV, V, VI, or VII.

10. The method of claim 7, wherein the CCHFV comprises IbAr 10200 or Afg09-2990.

11. A method of increasing the likelihood of survival or decreasing the likelihood or severity of at least one symptom from a Congo-Crimean Hemorrhagic Fever Virus (CCHFV) in a subject in need thereof, the method comprising administering to the subject a vaccine comprising a vector comprising 8.5 μmoles or more of the nucleic acid of SEQ ID NO: 3, and a promoter, wherein the nucleic acid of SEQ ID NO: 3 is operably linked to the promoter and wherein the administering provides at least a 60%, 70%, 80%, 90%, 95%, 96%, 97%, 98%, 99%, 99.8%, 99.9%, or 100% likelihood of survival in the subject five days after exposure to the CCHFV or the administering reduces the likelihood of a greater than 10% weight loss in the subject after exposure to the CCHFV.

12. The method of claim 11, wherein the administering comprises three doses of the vaccine, each dose being spaced at least 1, 2, 3, 4, 5, 6, 7, 8, 9, 10, 11, 12, 13, 14, 15, 16, 17, 18, 19, 20, or 21 days apart and each dose comprising 8.5 µmoles or more of the nucleic acid of SEQ ID NO: 3.

13. The method of claim 11, wherein the CCHFV is from Clade I, II, III, IV, V, VI, or VII.

14. The method of claim 11, wherein the CCHFV comprises IbAr 10200 or Afg09-2990.

15. A method of increasing the likelihood of survival or decreasing the likelihood or severity of at least one symptom from a Congo-Crimean Hemorrhagic Fever Virus (CCHFV) in a subject in need thereof, the method comprising administering to the subject a vaccine comprising a vector comprising a promoter and 0.385 µmoles or more of the nucleic acid of SEQ ID NO: 1 or SEQ ID NO: 3 per 1 gram of body weight of the subject, wherein the nucleic acid of SEQ ID NO: 1 or SEQ ID NO: 3 is operably linked to the promoter and wherein the administering provides at least a 60%, 70%, 80%, 90%, 95%, 96%, 97%, 98%, 99%, 99.8%, 99.9%, or 100% likelihood of survival in the subject five days after exposure to the CCHFV or the administering reduces the likelihood of a greater than 10% weight loss in the subject after exposure to the CCHFV.

16. The method of claim 15, wherein the administering comprises three doses of the vaccine, at least two of the doses being spaced at least 1, 2, 3, 4, 5, 6, 7, 8, 9, 10, 11, 12, 13, 14, 15, 16, 17, 18, 19, 20, or 21 days apart and each dose comprising 0.385 µmoles or more of the nucleic acid of SEQ ID NO: 1 per 1 gram of body weight of the subject.

17. The method of claim 15, wherein the CCHFV is from Clade I, II, III, IV, V, VI, or VII.

18. The method of claim 15, wherein the CCHFV comprises IbAr 10200 or Afg09-2990.

19. The method of claim 15, wherein the administering comprises three doses of the vaccine, each dose being spaced at least 1, 2, 3, 4, 5, 6, 7, 8, 9, 10, 11, 12, 13, 14, 15, 16, 17, 18, 19, 20, or 21 days apart and each dose comprising 0.385 µmoles or more of the nucleic acid of SEQ ID NO: 3 per 1 gram of body weight of the subject.

20. The method of claim 15, wherein the CCHFV is from Clade I, II, III, IV, V, VI, or VII.

21. The method of claim 15, wherein the CCHFV comprises IbAr 10200 or Afg09-2990.

22. A method of increasing the likelihood of survival or decreasing the likelihood or severity of at least one symptom from a Congo-Crimean Hemorrhagic Fever Virus (CCHFV) in a subject in need thereof, the method comprising administering to the subject an effective amount of a vaccine comprising a vector comprising a promoter and the nucleic acid of SEQ ID NO: 1, wherein the nucleic acid of SEQ ID NO: 1 is operably linked to the promoter and wherein the administering provides at least a 60%, 70%, 80%, 90%, 95%, 96%, 97%, 98%, 99%, 99.8%, 99.9%, or 100% likelihood of survival in the subject five days after exposure to the CCHFV or the administering reduces the likelihood of a greater than 10% weight loss in the subject after exposure to the CCHFV.

23. The method of claim 22, wherein the CCHFV is not IbAr 10200.

24. The method of claim 22, wherein the administering comprises three doses of the vaccine, each dose being spaced at least 1, 2, 3, 4, 5, 6, 7, 8, 9, 10, 11, 12, 13, 14, 15, 16, 17, 18, 19, 20, or 21 days apart.

25. The method of claim 22, wherein the CCHFV is from Clade I, II, III, IV, V, VI, or VII.

26. The method of claim 22, wherein the CCHFV comprises Afg09-2990.

27. The method of claim 22, wherein the effective amount comprises 0.385 µmoles or more of the nucleic acid of SEQ ID NO: 1 per 1 gram of body weight of the subject.

\* \* \* \* \*